(12) United States Patent
Tovar et al.

(10) Patent No.: US 9,334,304 B2
(45) Date of Patent: May 10, 2016

(54) SELF-ASSEMBLING PEPTIDES BEARING ORGANIC ELECTRONIC FUNCTIONALITY AND APPLICATIONS EMPLOYING THE SAME

(75) Inventors: John Dayton Tovar, Baltimore, MD (US); Stephen Robert Diegelmann, Baltimore, MD (US); Brian D. Wall, Baltimore, MD (US); Geeta Sophie Vadehra, Los Angeles, CA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 797 days.

(21) Appl. No.: 13/262,742

(22) PCT Filed: Apr. 2, 2010

(86) PCT No.: PCT/US2010/029747
§ 371 (c)(1),
(2), (4) Date: Jan. 13, 2012

(87) PCT Pub. No.: WO2010/115080
PCT Pub. Date: Oct. 7, 2010

(65) Prior Publication Data
US 2012/0101022 A1    Apr. 26, 2012

Related U.S. Application Data

(60) Provisional application No. 61/202,772, filed on Apr. 2, 2009.

(51) Int. Cl.
*A61K 49/00* (2006.01)
*C07K 7/02* (2006.01)
*C07K 7/06* (2006.01)
*C07K 5/103* (2006.01)
*A61L 27/22* (2006.01)
*A61L 27/38* (2006.01)
*C07K 5/107* (2006.01)

(52) U.S. Cl.
CPC ........... *C07K 5/1008* (2013.01); *A61K 49/0056* (2013.01); *A61L 27/227* (2013.01); *A61L 27/38* (2013.01); *C07K 5/1016* (2013.01); *C07K 7/06* (2013.01); *C07K 7/02* (2013.01)

(58) Field of Classification Search
CPC ........... A61K 49/0056; A61K 49/0052; A61K 49/0021; A61K 49/005; C07K 5/1008; C07K 5/1005; C07K 5/101; C07K 5/1013; C07K 17/02
See application file for complete search history.

(56) References Cited

U.S. PATENT DOCUMENTS

2004/0001893 A1*  1/2004  Stupp et al. .................... 424/488
2005/0129615 A1*  6/2005  Rozga et al. .................. 424/1.49
2008/0177033 A1   7/2008  Stupp et al.

FOREIGN PATENT DOCUMENTS

WO    2004039862 A1    5/2004

OTHER PUBLICATIONS

Klok et al., "Synthesis of a silk-inspired peptide—oligothiophene conjugate", Org. Biomol. Chem, 2004, pp. 3541-3544.*
Guler et al., "Presentation of RGDS Epitopes on Self-Assembled Nanofibers of Branched Peptide Amphiphiles", Biomacromolecules, 2006, pp. 1855-1863.*
Matmour et al., "Oligo(p-phenylenevinylene)-Peptide Conjugates: Synthesis and Self-Assembly in Solution and at the Solid-Liquid Interface"; JACS, published on the web Oct. 11, 2008; pp. 14576-14583.*
Tan et al.,"Novel Carboxylated Oligothiophenes as Sensitizers in Photoelectric Conversion Systems", Chem. Eur. J. 2005, pp. 6272-6276.*
Steullet et al., "Design, Synthesis and DNA-Cleavage of Gly-Gly-His-Naphthalene Diimide Conjugates", Bioorganic and Medicinal Chemistry Letters, 1999, pp. 2935-2940.*
Koynov et al., "Diffusion and Conformation of Peptide-Functionalized Polyphenylene Dendrimers Studied by Fluorescence Correlation and 13C NMR Spectroscopy", Biomacromolecules (2007) pp. 1745-1750.*
Ahn et al. "Soluble polymer-supported convergent parallel library synthesis", Chemical Communications, 2003, pp. 480-481.*
Miller et al. "The Synthesis and Screening of 1,4,5,8-Naphthalenetetracarboxylic Diimide-Peptide Conjugates with Antibacterial Activity", Bioorgnaic & Medicinal Chemistry, 2001, pp. 2015-2024.*
Ulysse L., et al., Bioorg Med. Chem. Lett., 1994, 4, 2145.
Schillinger E.K., et al., Adv. Mater., 2009, 21, 1562; D. A. Stone, L. Hsu and S. I. Stupp, Soft Matter, 2009, 5, 1990.
Roverto P., et al., Lett. Pept. Sci., 1995, 2, 27.

(Continued)

*Primary Examiner* — Lianko Garyu
(74) *Attorney, Agent, or Firm* — Ward and Smith, P.A.

(57) ABSTRACT

The aqueous self-assembly of oligopeptide-flanked π-conjugated molecules into discrete one-dimensional nanostructures is described. Unique to these molecules is the fact that the π-conjugated unit has been directly embedded within the peptide backbone by way of a synthetic amino acid with π-functionality that is compatible with standard Fmoc-based peptide synthesis or by way of a diacid or other bis(electrophile) that can covalently cross-link peptide chains presented on a synthesis support. The peptide-based molecular designs enforce intimate π-π communication within the aggregates after charge-screening and self-assembly, making these nanostructures attractive for optical or electronic applications in biological environments. In other embodiments, a convenient method to incorporate π-electron units into peptides that assemble into amyloid-like supramolecular polymers is disclosed. Self-assembly manipulates these "electronic peptides" into delocalized sub-10 nm one dimensional (1-D) nanostructures under completely aqueous conditions.

17 Claims, 15 Drawing Sheets

(56) References Cited

OTHER PUBLICATIONS

Ladame S., et al., Org. Lett, 2002, 4, 2509.
Biernat M., et al., Bioconjugate Chem., 2006, 17, 1116.
Wurthner F., Chem. Commun., 2004, 1564.
Cotlet M., et al., J. Am. Chem. Soc., 2005, 127, 9760.
Levin S., et al., J. Am. Chem. Soc., 2007, 129, 13043.
Freire F., et al., J. Am. Chem. Soc., 2009, 131, 7970.
Aggeli A., et al., Nature, 1997, 386, 259.
Qu Y., et al., J. Am. Chem. Soc., 2000, 122, 5014.
Hartgerink J.D., et al., Science, 2001, 294, 1684.
Pochan D.J., et al., J. Am. Chem. Soc., 2003, 125, 11802.
Aggeli A., et al., Proc. Nat. Acad. Sci. USA, 2001, 98, 11857.
Venyaminov S.Y., et al., Anal. Biochem., 1991, 198, 250.
Schoonbeek, F., et al., Angew. Chem., Int. Ed. 1999 38 1393-1397.
Hill, J., et al., Science 2004 304 1481-1483.
Leclere, P., et al., Chem. Mater. 2004 16 4452-4466.
Hoeben, F., et al., J. Chem. Rev. 2005 105 1491-1546.
Jahnke, E., et al., Angew. Chem., Int. Ed. 2006 45 5383-5386.
Li, X., et al., Chem. Commun. 2006 n/a 3871-3873.
Che, Y., et al., J. Am. Chem. Soc. 2007 129 7234-7235.
Ryu, J., et al., Chem. Commun. 2008 n/a 1043-1054.
Wang, Q., et al., Angew. Chem., Int. Ed. 2002 41 459-462.
Kas, O., et al., Chem. Mater. 2006 18 4238-4245.
Lahann, J., et al., Science 2003 299 371-374.
Langer, R. MRS Bull. 2006 31 477-485.
Klok, H., et al., Org. Biomol. Chem. 2004 2 3541-3544.
Kong, X., et al., Macromolecules 2004 37 8180-8183.
Ashkenasy, N., et al., Small 2006 2 99-102.
Schmidt C., et al., Proc. Natl. Acad. Sci. U.S.A. 1997 94 8948-8953.
Wallace, G., et al., Soft Matter 2007 3 665-671.
Lashuel, H., et al., J. Am. Chem. Soc. 2000 122 5262-5277.
MacPhee, C., et al., J. Am. Chem. Soc. 2000 122 12707-12713.
Zhang, S., et al., Proc. Nat. Acad. Sci.U.S.A. 1993 90 3334-3338.
Collier, J., et al., Adv. Mater. 2004 16 907-910.
Haines, L., et al., J. Am. Chem. Soc. 2005 127 17025-17029.
Smeenk, J., et al., Angew. Chem., Int. Ed. 2005 44 1968-1971.
Davies, R., et al., Supramol. Chem. 2006 18 435-443.
Wang, W., et al., J. Am. Chem. Soc. 2003 125 5248-5249.
Gothard, C., et al., J. Am. Chem. Soc. 2007 129 7272-7273.
Cornil, J., et al., J. Am. Chem. Soc. 1998 120 1289-1299.
Schenning, A., et al., J. Am. Chem. Soc. 2001 123 409-416.
Whitehouse, C., et al., Angew. Chem., Int. Ed. 2005 44 1965-1968.
Kayser, V., et al., J. Am. Chem. Soc. 2004 126 336-343.
Mesquida, P., et al., J. Mater. Sci. Mater. Med. 2007 18 1325-1331.
Rubin, N., et al., J. Am. Chem. Soc. 2008 130 4602-4603.
Li, L., et al., Angew. Chem., Int. Ed. 2007 46 5873-5876.
Mokhir, A., et al., Bioorganic & Medicinal Chemistry Letters, 2003, 13, 2489-2492.
Ni, Z., et al., J. Am. Chem. Soc., 2005, 127, 12752-12753.
Li, Z., et al., Org. Lett., 2007, 9, 3659-3662.
Sancho-Garcia, J., et al., J. Phys. Chem. B, 2005, 109, 4872-4880.
Hou, J., et al., J. Am. Chem. Soc., 2006, 128, 4911-4916.
Stone, D., et al., Soft Matter, 2009, 5, 1990.
Kranich, R., et al., J. Med. Chem. 2007, 50, 1101-1115.
Messmore, B., et al., J. Am. Chem. Soc., 2004, 126, 14452.
Chen, J., et al., J. Am. Chem. Soc., 2008, 130, 16496.
Mahesh, S., et al., Chem. Commun., 2009, 5984.
Shao, H., et al., J. Am. Chem. Soc., 2009, 131, 16374.
Channon, K., et al., Soft Matter, 2008, 4, 647.
Cherny, I., et al., Chem. Int. Ed., 2008, 47, 4062.
Miller, R., et al., J. Am. Chem. Soc., 2007, 129, 3104.
Channon, K., et al., J. Am. Chem. Soc., 2008, 130, 5487.
Matmour, R., et al., J. Am. Chem. Soc., 2008, 130, 14576.
Smith, A., et al., Adv. Mater., 2008, 20, 37.
Farrall et al., "Reaction of Cross-linked Chloromethyl Polystyrene with 1,4-Butanedithiol: Site-Site Interactions and Their Control," J. Am. Chem. Soc., 100:25, 1978, pp. 7998-7999.
Diegelmann S.R., et al., "One-dimensional optoelectronic nanostructures derived from the aqueous self-assembly of r-conjugated oligopeptides", J. Am. Chem. Soc., 2008, vol. 130, pp. 13840-13841. See abstract and p. 13841 right column.
Gus'Kova O.A., et al., "Silk-inspired 'molecular chimeras': atomistic simulation of nanoarchitectures based on thiophene-peptide copolymers" Chem. Phys. Letters, 2008, vol. 461, pp. 64-70. See abstract and scheme 1.
Barbarella G., et al., "The versatile thiophene: an overview of recent research on thiophene-based materials", Adv. Mater., 2005, vol. 17, pp. 1581-1593. See abstract and Fig. 1.

\* cited by examiner

Peptide 1: (GAFDV)-NDI-(GAFDV) (n=0)
Peptide 2: (GAFDV)-PDI-(GAFDV) (n=1)

Peptide 3: (GAFD)-OT3-(GAFD) (n=0)
Peptide 4: (GAFD)-OT4-(GAFD) (n=1)

Peptide 5: (GAFD)-OP2-(GAFD)

Peptide 6: (GAVEV)-OPV3-(GAVEV)

Peptide 7: (AAFD)-OPV3-(AAFD)

Peptide 8: (FAFD)- OPV3-(FAFD)

SELF-ASSEMBLING PEPTIDES BEARING ORGANIC ELECTRONIC FUNCTIONALITY AND APPLICATIONS EMPLOYING THE SAME

CROSS-REFERENCE TO RELATED APPLICATIONS

This application is a 35 U.S.C. 371 U.S. national entry of International Application PCT/US10/29747 having an international filing date of Apr. 2, 2010, which claims the benefit of U.S. Provisional Application No. 61/202,772, filed Apr. 2, 2009, the content of each of the aforementioned applications is herein incorporated by reference in its entirety.

FEDERALLY SPONSORED RESEARCH OR DEVELOPMENT

This invention was made in part with United States Government support under DGE-0549350 awarded by the National Science Foundation. The U.S. Government has certain rights in the invention.

BACKGROUND

Pi-conjugated supramolecular structures have many useful physico-chemical properties, but their usefulness in biological and medical applications has been limited due to generally poor water solubility and toxicity caused by current assembly processes. Approaches known in the art for assembling π-conjugated supramolecular structures typically involve solvating the organic electronic material in a toxic organic solvent. In other approaches, organic electronic structures are rendered water soluble by substituents that, in effect, repel biological interaction, e.g., resist biological adhesion. Water-soluble conjugated polymers bearing ionic groups or those prepared in the presence of ionic surfactants can impart useful electronic properties in aqueous environments, but usually form amorphous bulk films when processed with little control of intermolecular or interpolymer order on nanoscale dimensions. Thus, the construction of discrete organic electronic nanostructures with biologically interactive function in aqueous and/or physiological environments remains a challenge.

SUMMARY

The presently disclosed subject matter provides compositions comprising one or more π-conjugated oligopeptides having a general structure of peptide-[(organic electronic unit)-peptide]$_n$, wherein the organic electronic unit is selected from the group consisting of an electroactive material, a chromophore, a fluorescent material, and/or a material having an environmentally sensitive optoelectronic property; and each peptide can be the same or different and comprises from 2 to 100 amino acid residues. In particular embodiments, the organic electronic unit is selected from the group consisting of an α-oligothiophene, an oligophenylene, an oligo(p-phenylene vinylene), a rylene, and diimides and diacids, thereof. The peptide can be any naturally occurring amino acid or variant thereof.

In some aspects, the presently disclosed peptide-[organic electronic unit]-peptide structure has the property of self assembly into a defined nanostructure when combined with identical or different peptide-[organic electronic unit]-peptide structures under aqueous or physiological conditions. In certain aspects, the defined nanostructure has an electrical property, an optoelectronic property, and/or a cell adhesion property.

In other aspects, the presently disclosed defined nanostructures can be used as a cell growth and/or cell adhesion scaffold to induce selective tissue growth in a subject. In yet further aspects, the presently disclosed defined nanostructures can be used as an electrically conductive implant in a subject, an implantable medical device, and/or an in vivo or in vitro biological sensor.

In yet other aspects, the presently disclosed subject matter provides methods for preparing such π-conjugated oligopeptides and defined nanostructures comprising the same.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
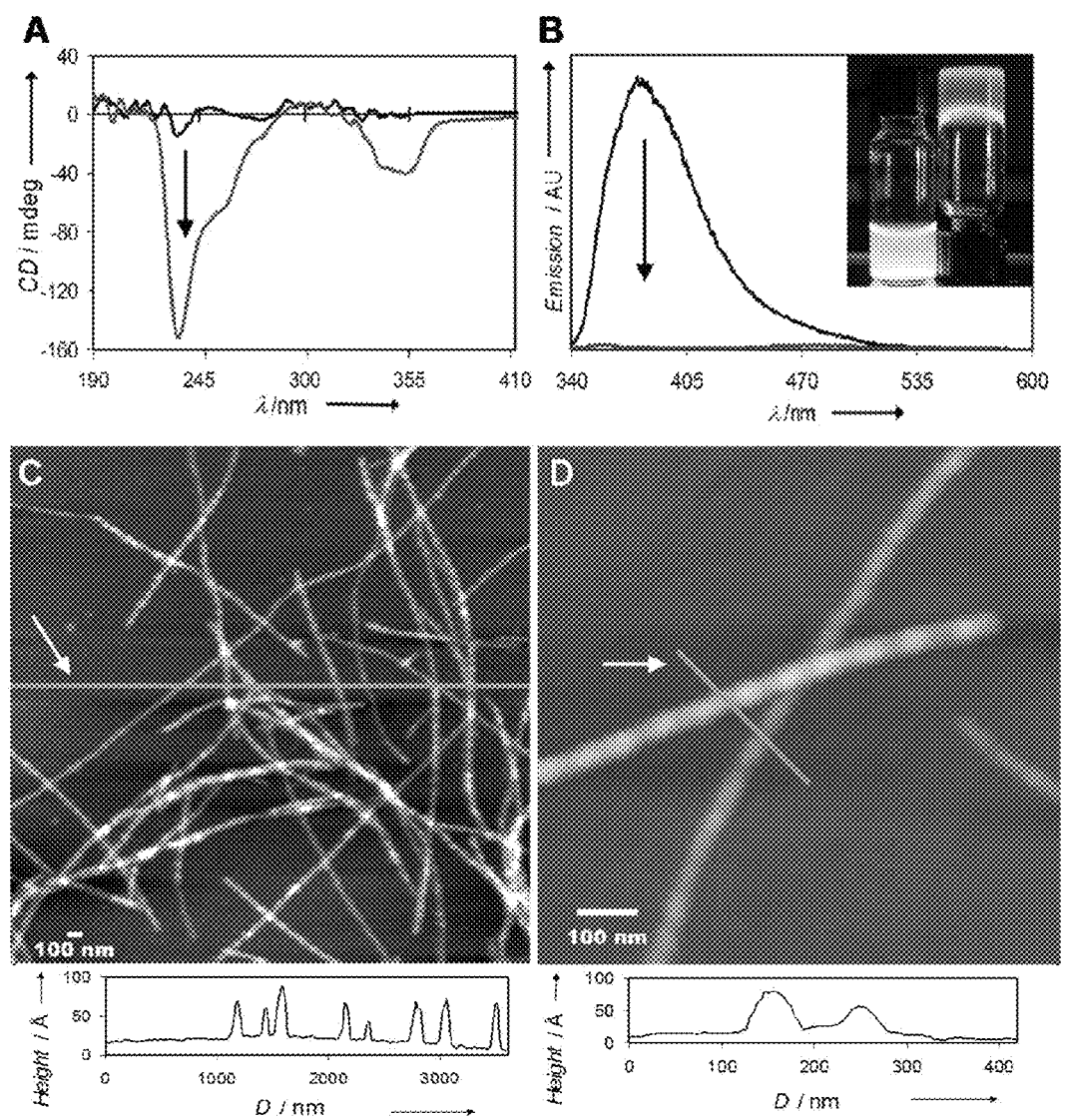
Figure 2:
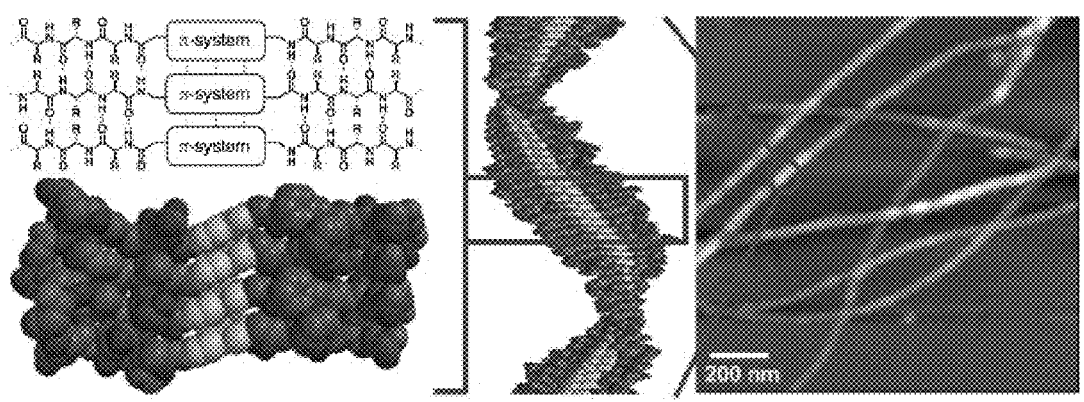
Figure 3:
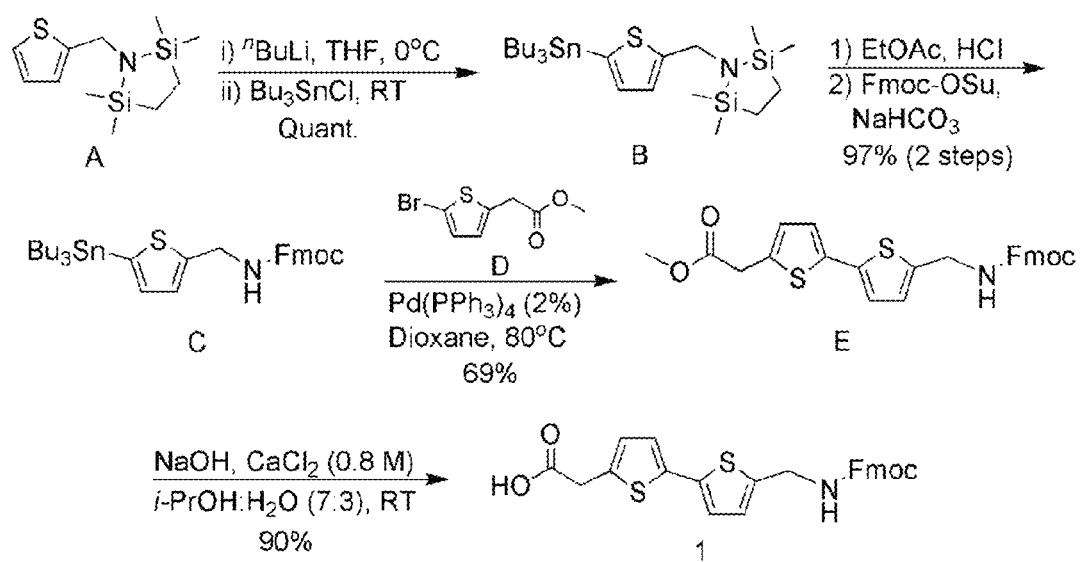
Figure 4:
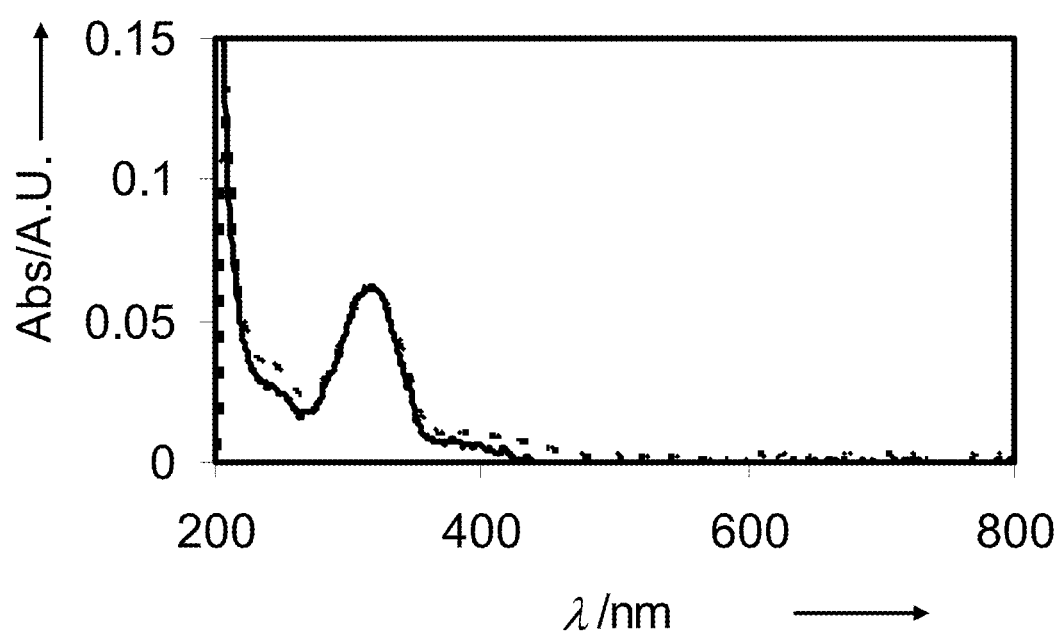
Figure 5A:
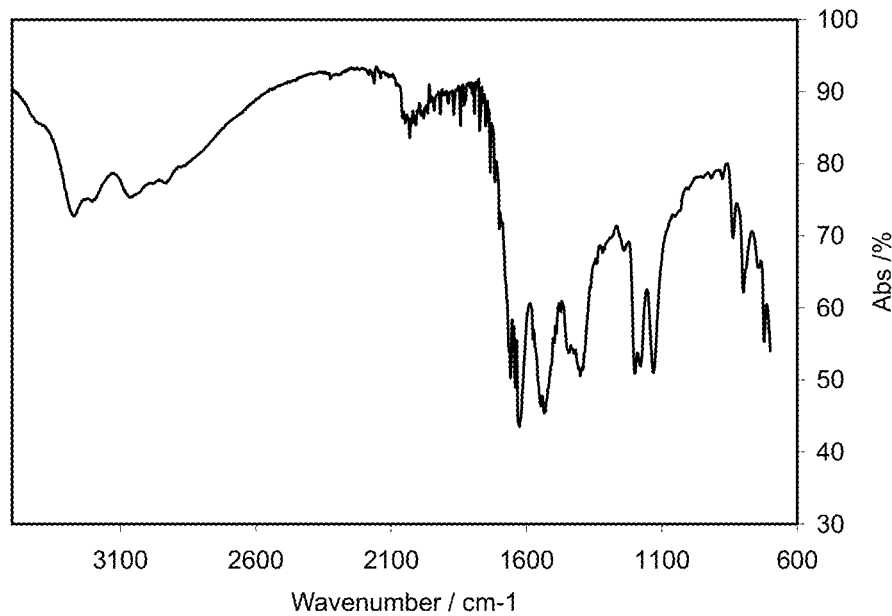
Figure 5B:
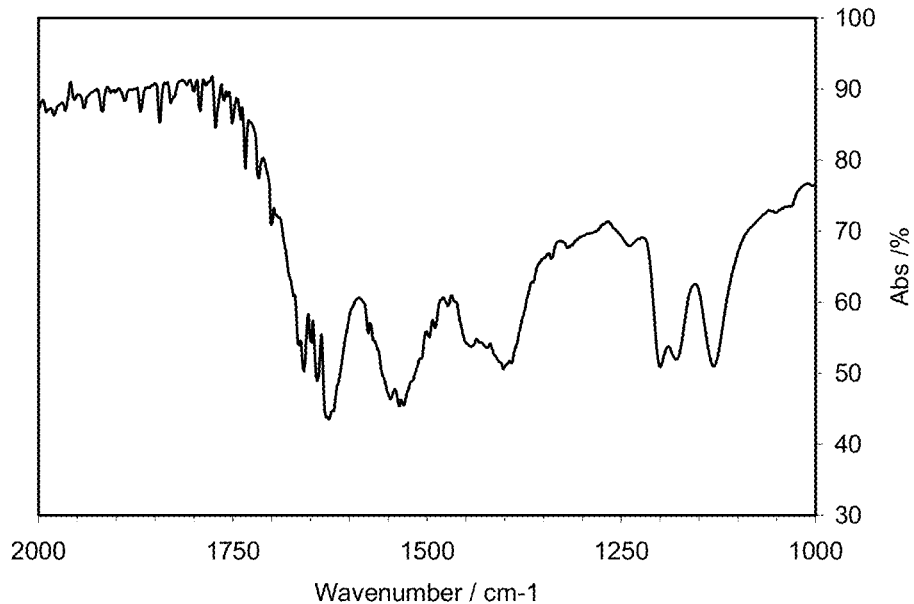
Figure 5C:
Figure 5D:
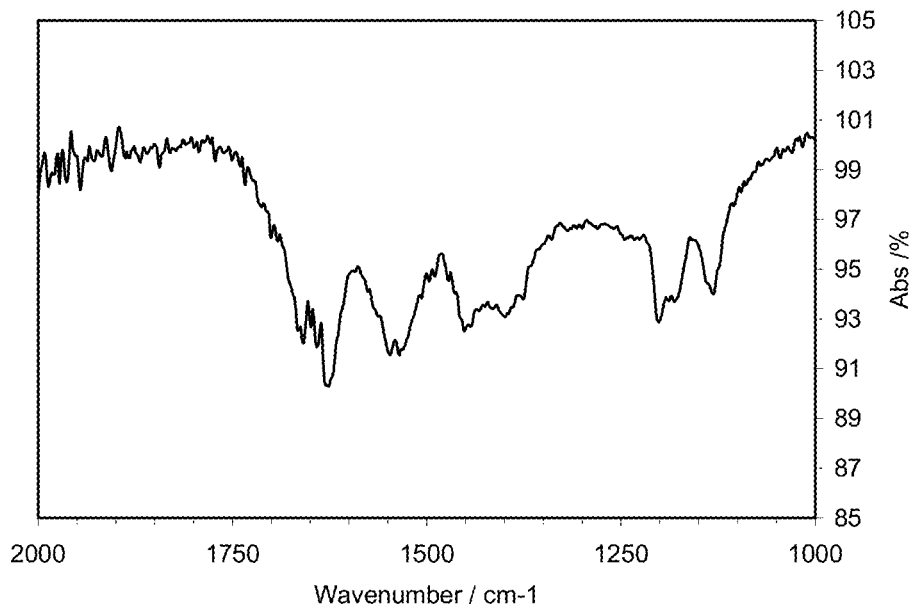
Figure 6A:
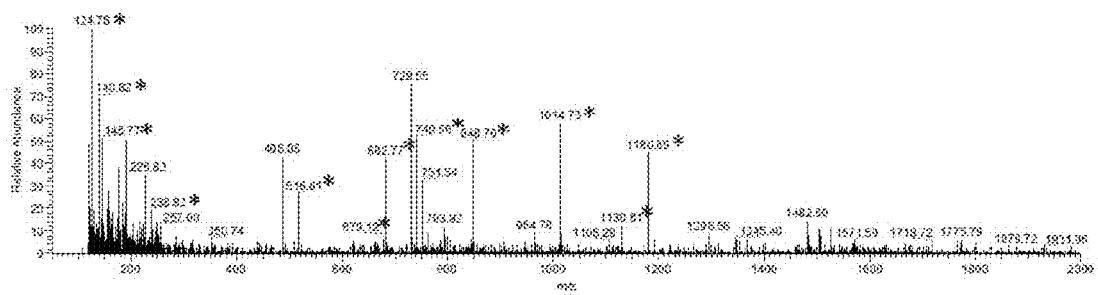
Figure 6B:
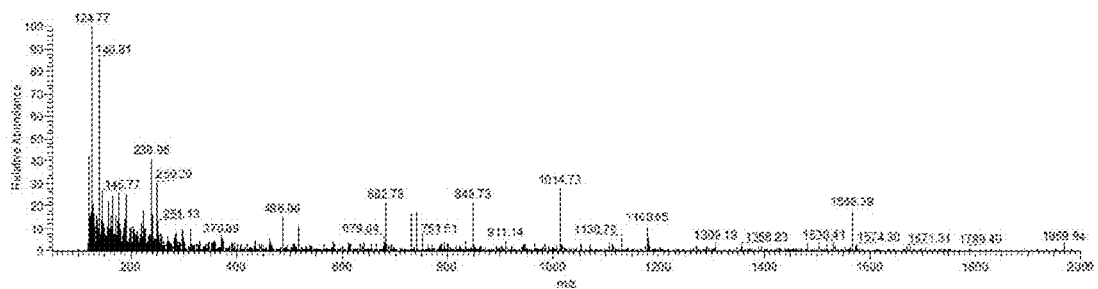
Figure 7:
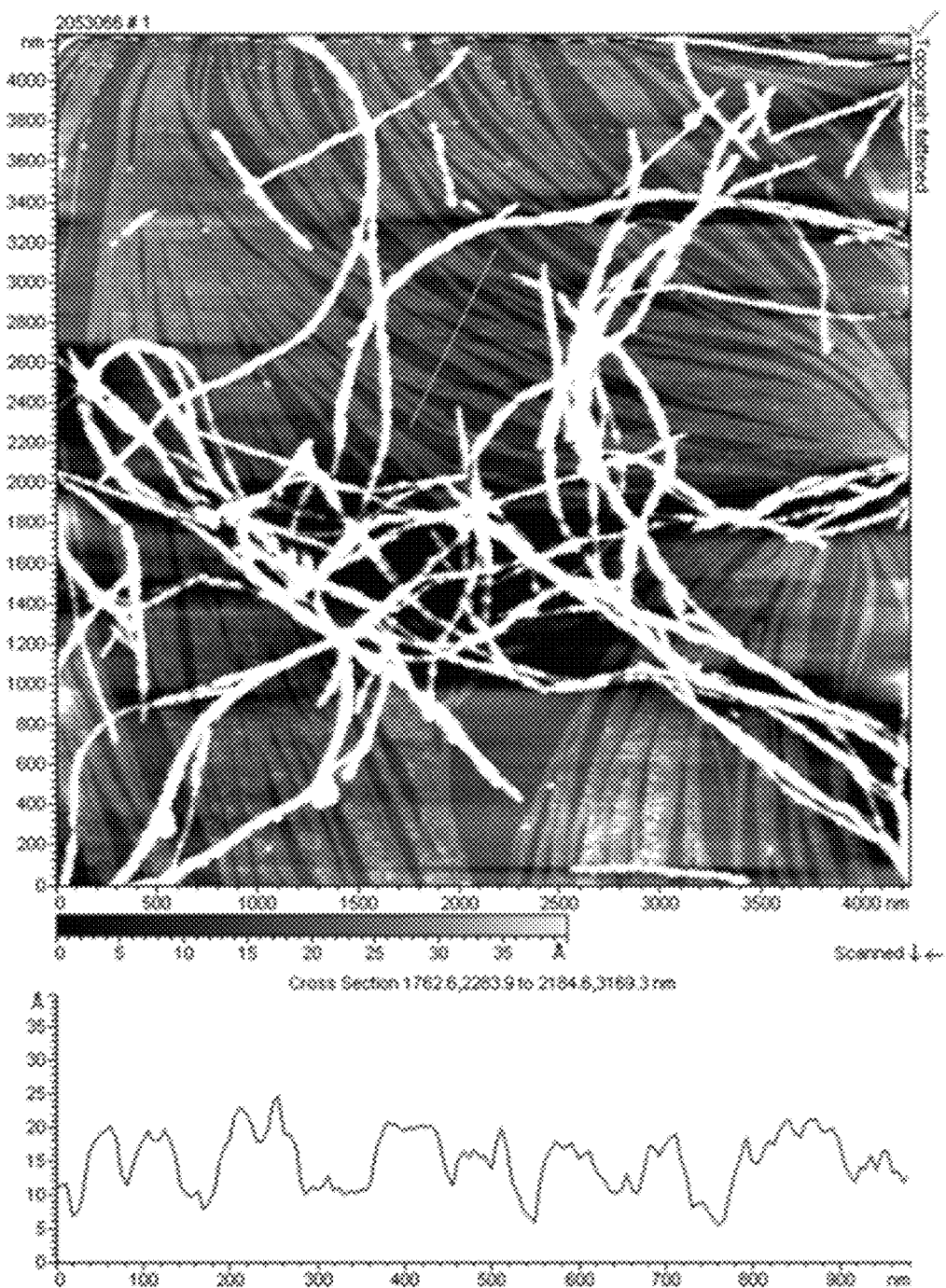
Figure 8:
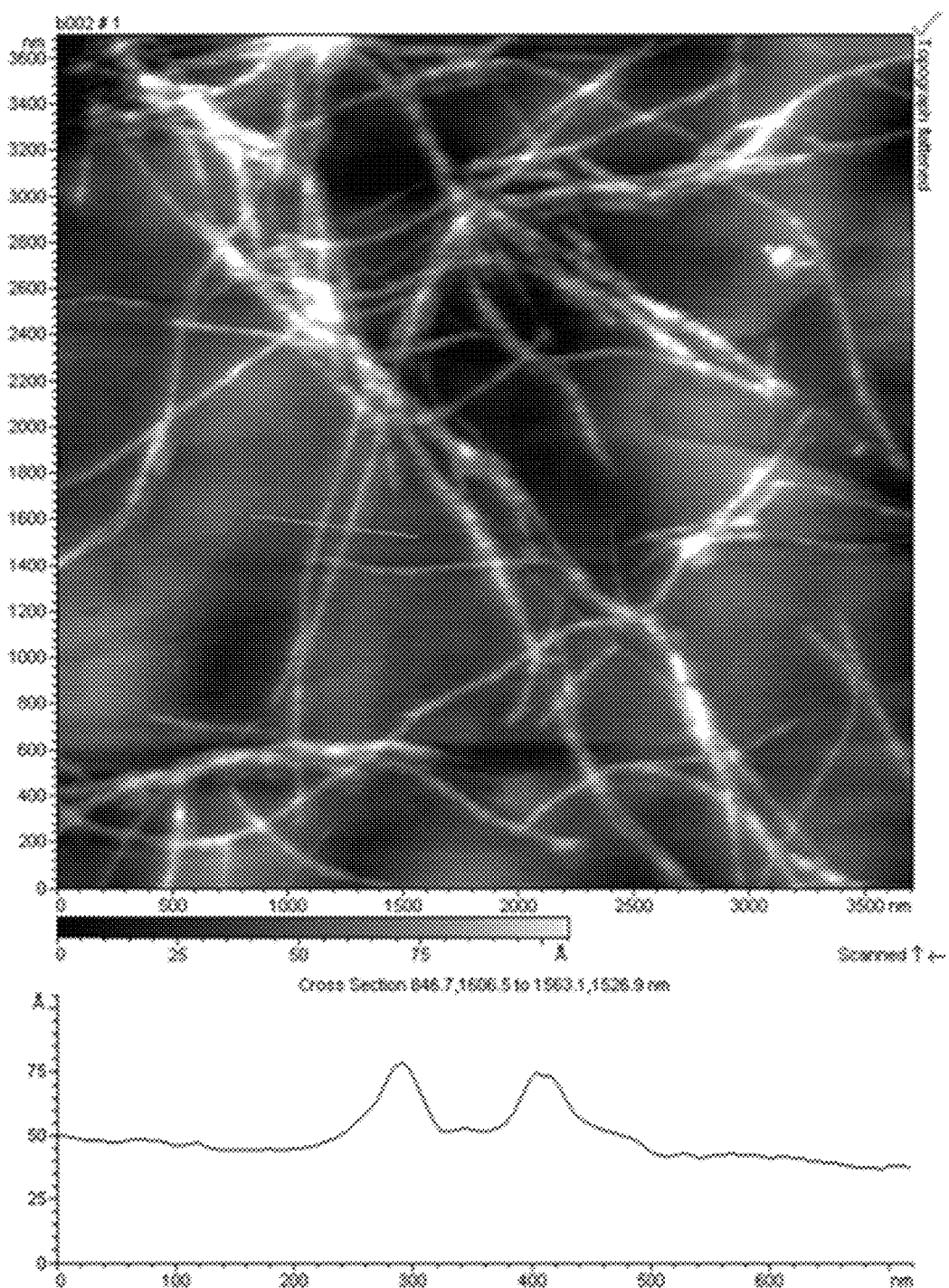
Figure 9:
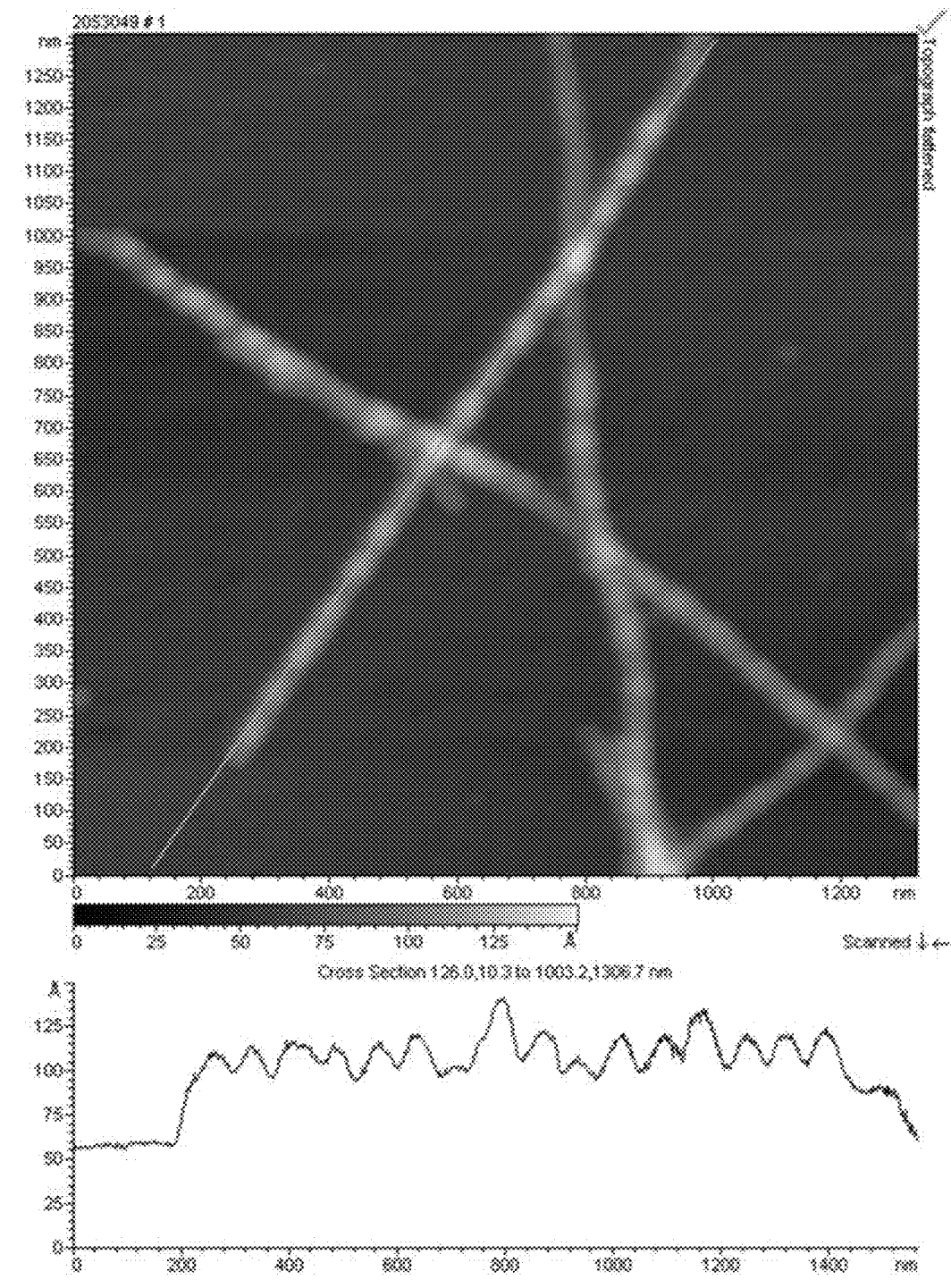
Figure 10:
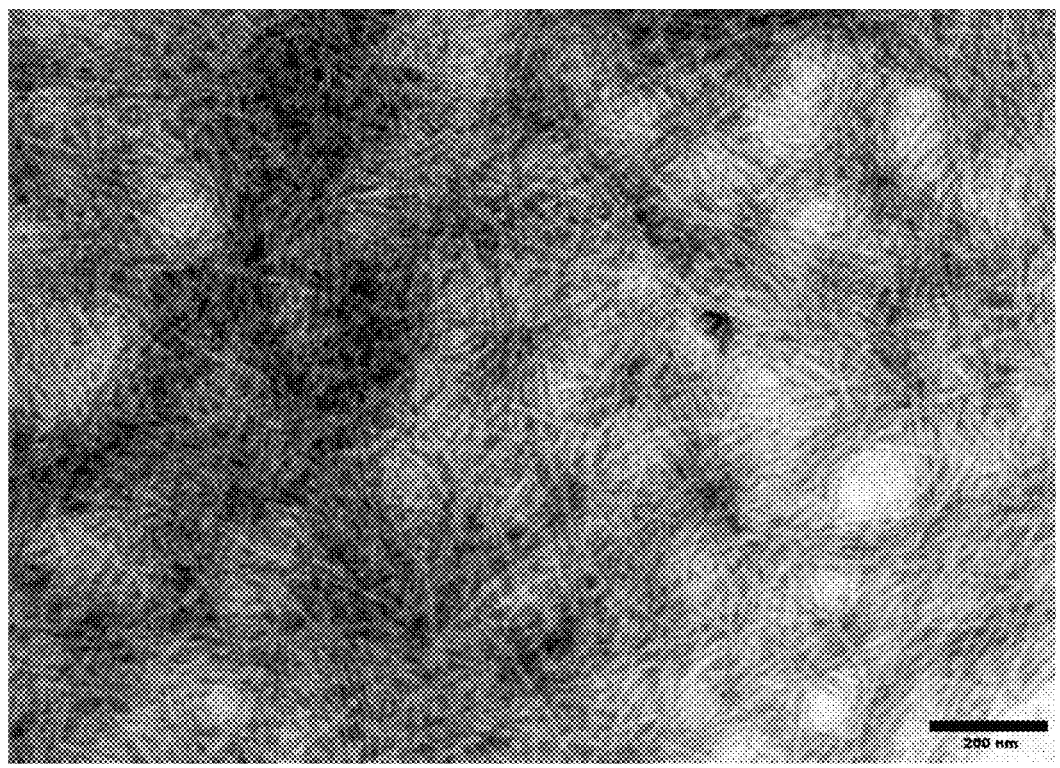
Figure 11:
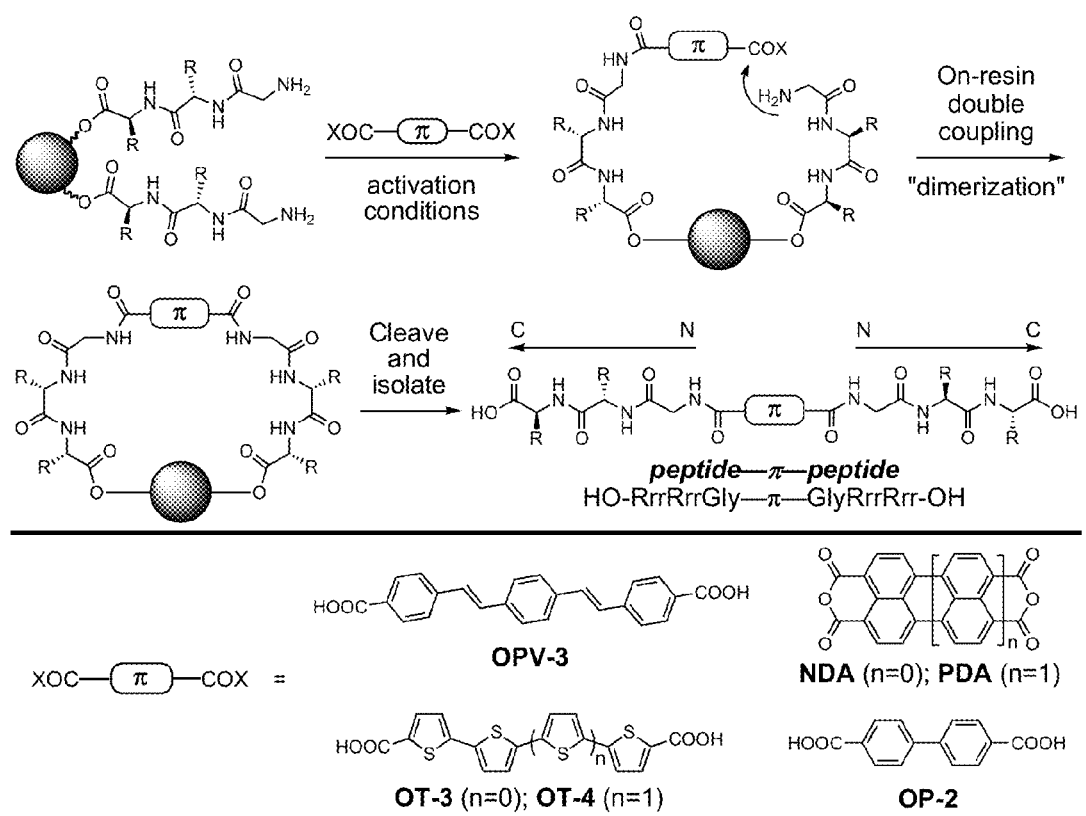
Figure 12:
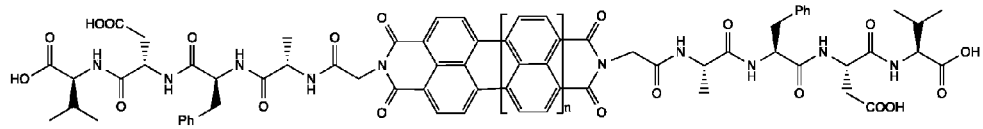
Figure 12:
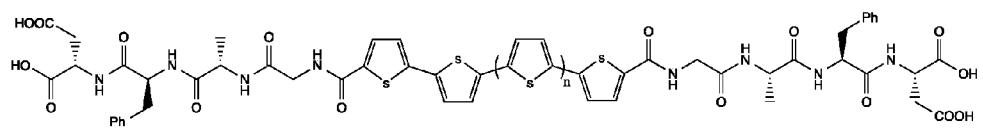
Figure 12:
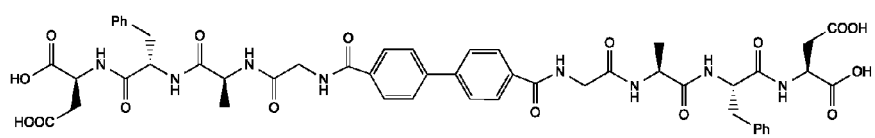
Figure 12:
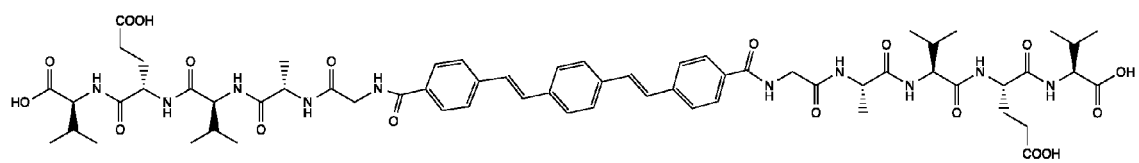
Figure 12:
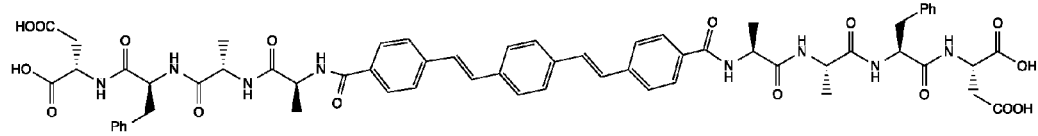
Figure 12:
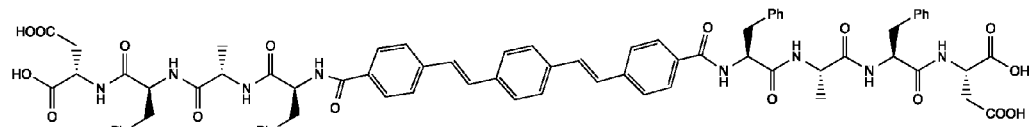
Figure 13:
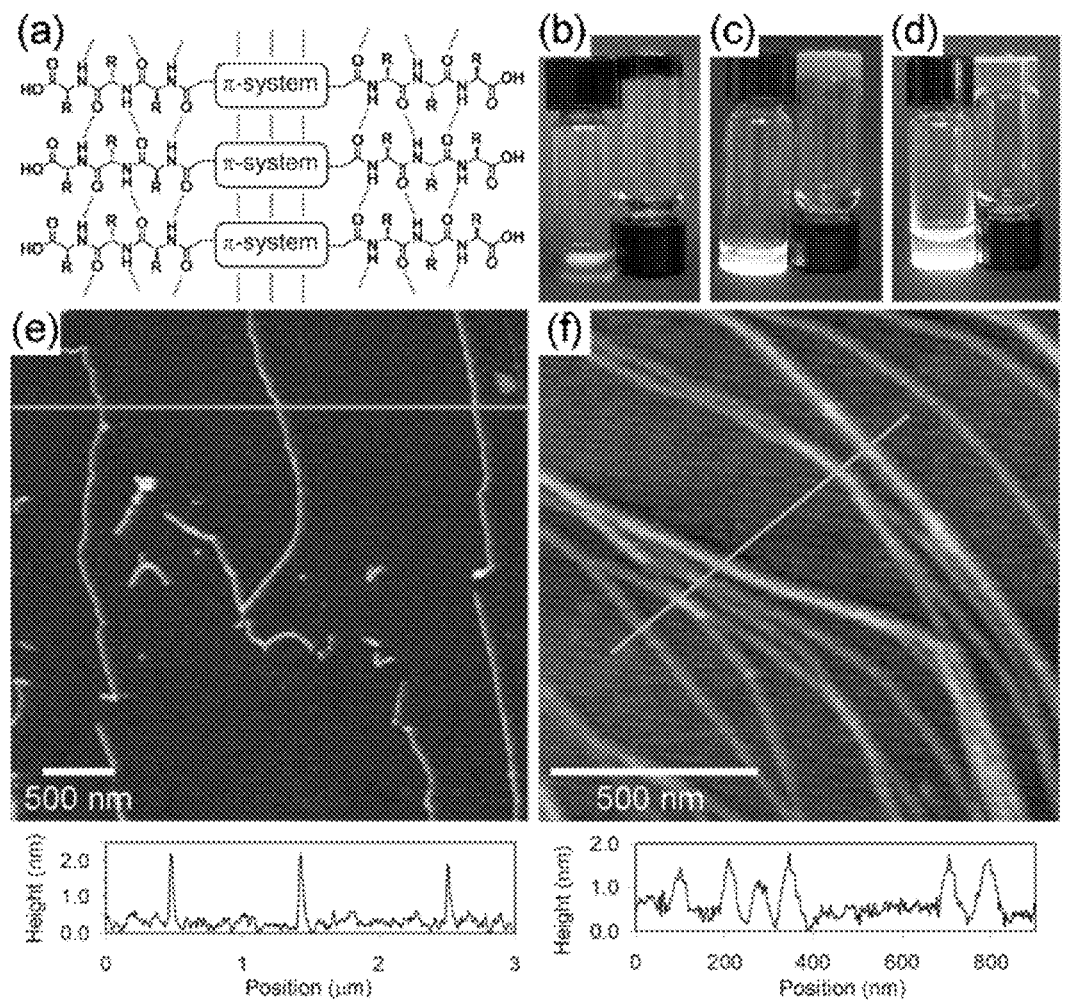

Having thus described the presently disclosed subject matter in general terms, reference will now be made to the accompanying Drawings, which are not necessarily drawn to scale, and wherein:

FIGS. 1A and 1B are (A) circular dichroism (CD) and (B) fluorescence spectra of compound 2 in basic (dissolved) and acidic (assembled) aqueous solutions, where the arrow denotes the spectral change upon acidification. The inset of panel B depicts a concentrated solution (left) and a gel (right) irradiated at 365 nm;

FIGS. 1C and 1D are tapping-mode atomic force microscope (AFM) images and height profiles of the indicated line trace of (C) large area and (D) isolated structures formed after assembly and deposition on freshly cleaved mica surfaces;

FIG. 2 is an energy-minimized illustration of β-sheets and π-stacks as line drawings and space-filling models (left) and the helical twist sense along a model aggregate (center, hydrogens omitted), and the supramolecular aggregates resulting from assembly (right);

FIG. 3 is a scheme showing the total synthesis of bithiophene-based amino acid 1;

FIG. 4 shows UV-Vis spectra of compound 2 taken in basic water (conditions that foster dissolution, pH 7, solid line) and acidic water (conditions that foster aggregation, pH −1, dashed line);

FIGS. 5A-5D are attenuated total reflectance (ATR) infrared (IR) spectra of compound 2 in the solid state (A and B) and mineral oil mull (C and D);

FIGS. 6A and 6B are electrospray ionization (ESI−) mass spectra of compound 2: In (A) the asterisks indicate mass peaks that are observable in background spectra. Background spectrum for compound 2 (B) is shown because of a large number of background peaks;

FIG. 7 is an AFM image of compound 2 on mica substrate showing the formation of 1-D nanostructures on top of a surface passivated with flat tape-like structures. The height profile of the tape-like structures shows heights of approximately 1 nm;

FIG. 8 is an AFM image of compound 2 on a graphite substrate showing the formation of 1-D nanostructures and lack of flat tape-like structures;

FIG. 9 is the height profile along the long axis of 1-D nanostructures derived from compound 2, which show regular height fluctuations. Average spacing of height fluctuations of indicated structures is 76 nm;

FIG. 10 is a transmission electron microscopy (TEM) image of compound 2 on formvar/carbon coated grids showing the formation of 1-D nanostructures. Sample was analyzed at 100 kV and a magnification of 86000×;

FIG. 11 is a schematic representation of the presently disclosed on-resin cross-linking of immobilized peptide chains via amidation or imidation of π-conjugated dielectrophiles. Activation conditions: pyridine and i-Pr$_2$NEt at reflux (for NDA/PDA) or PyBOP and i-Pr$_2$NEt in NMP/CH$_2$Cl$_2$ (for OPV/OT/OP);

FIG. 12 is a series of peptide-[organic electronic unit]-peptide conjugates prepared via the presently disclosed on-resin dimerization; Peptide 1, GAFDV (SEQ ID NO:1) is attached through the N-terminus to the carboxyl groups of NDI; Peptide 2, GAFDV (SEQ ID NO:1) is attached through the N-terminus to the carboxyl groups of PDI; Peptide 3, GAFD (SEQ ID NO:2) is attached through the N-terminus to the carboxyl groups of OT3; Peptide 4, GAFD SEQ ID NO:2) is attached through the N-terminus to the carboxyl groups of OT4; Peptide 5, GAFD (SEQ ID NO:2) is attached through the N-terminus to the carboxyl groups of OP2; Peptide 6, GAVEV (SEQ ID NO:3) is attached through the N-terminus to the carboxyl groups of OPV3; Peptide 7, AAFD (SEQ ID NO:4) is attached through the N-terminus to the carboxyl groups of OPV3; Peptide 8, FAFD (SEQ ID NO:5) is attached through the N-terminus to the carboxyl groups of OPV3;

FIG. 13a is an illustration of a parallel β-sheet network within an aggregate;

FIGS. 13b-13d are representative photographs of molecularly dissolved aqueous peptide solutions (left sides) and of hydrogels formed after assembly (right sides) for peptides 2, 3 and 6 during irradiation with 365 nm light;

FIGS. 13e and 13f are tapping-mode atomic force microscopy (AFM) images obtained from assembled samples of peptides 2 (e, large area) and 3 (f, zoom in) as deposited on mica. Line profiles of the z-axis height are depicted below each image; and FIGS. 14a-14d are representative spectroscopic data for the presently disclosed peptides in their molecularly dissolved (basic pH, dashed line) and self-assembled (acidic pH, solid line) states in water: UV-vis and fluorescence (a,b) and circular dichroism (c,d) for peptides 3 (a,c) and 6 (b,d). The X (c,d) indicates unavoidable scattering at the spectroscopic concentrations required for measurement.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

I. Overview of Self-Assembling Peptides Having π-Electron Functionality

Self-assembling supramolecular materials with π-electron functionality are of increasing interest for nanotechnology, including emerging bionanotechnology. See, for example, Schoonbeek, F. S., et al., *Angew. Chem., Int. Ed.* 38:1393-1397 (1999); Hill, J. P., et al., *Science* 304:1481-1483 (2004); Leclere, P., et al., *Chem. Mater.* 16:4452-4466 (2004); Hoeben, F. J. M., et al., *J. Chem. Rev.* 105: 1491-1546 (2005); Jahnke, E., et al., *Angew. Chem., Int. Ed.* 45:5383-5386 (2006); Li, X. Q., et al., *Chem. Commun.* 3871-3873 (2006); Che, Y. K., et al., *J. Am. Chem. Soc.* 129:7234-7235 (2007); Ryu, J.-H., et al., *Chem. Commun.* 1043-1054 (2008); Schenning, A., et al., *J. Am. Chem. Soc.,* 123:409 (2001); Messmore, B. W., et al., *J. Am. Chem. Soc.* 126:14452 (2004); Li, X. Q., et al., *Chem. Commun.* 3871-3873 (2006); Chen, J. and McNeil, A. J., *J. Am. Chem. Soc.* 130:16496 (2008); Mahesh, S., et al., *Chem. Commun.* 5984 (2000); and Shao, H., et al., *J. Am. Chem. Soc* 131:16374 (2009). Self-assembling peptides are useful platforms for advanced nanomaterials, Channon, K. and MacPhee, C. E., *Soft Matter* 4:647 (2008); Cherny, I. and Gazit, E., *Angew. Chem. Int. Ed.,* 47:4062 (2008), but their potential as electronic materials has been tempered by the synthetic complexity needed to incorporate electronic functions into biological motifs.

The severe hydrophobicity of π-electron materials makes work in aqueous, e.g., physiologically relevant, media difficult. The vast majority of the approaches known in the art for preparing such materials involve the association of molecular components in organic solvents. Notable exceptions to these approaches include water-soluble rod-coil oligophenylenes, but these compounds are rendered soluble by oligo(ethylene oxide)s, which are known in many cases to resist specific biological adhesion. Ryu, J.-H., et al., supra.

Fluorophores, or other π-conjugated units, typically are installed onto proteins via side-chain covalent chemistry, such as lysine amidation, Michael-type cysteine addition, or through attachment at peptide termini. See Kas, O. Y., et al., *Chem. Mater.* 18:4238 (2006); Miller, R. A., et al., *J. Am. Chem. Soc.* 129:3104 (2007); Channon, K. J., *J. Am. Chem. Soc.* 130:5487 (2008); Matmour, R., *J. Am. Chem. Soc.* 130: 14576 (2008); Smith, A. M., *Adv. Mater.* 20:37 (2008). Methods for incorporation of π-conjugated units within the peptide backbone, however, are much rarer and have recently generated attention.

The inherent difficulty of incorporating π-conjugated units within the peptide backbone is evident by the fact that approaches known in the art typically involve a single highly specialized π-electron peptide linker. Pi-conjugated "amino acids" have been used directly for solid-phase peptide synthesis (SPPS), see Ulysse, L. and Chmielewski, J., *Bioorg Med. Chem. Lett.* 4:2145 (1994); Gothard, C. M., *J. Am. Chem. Soc.* 129:7272 (2007), but they require lengthy organic syntheses. Further, complex π-conjugated amino acids can be plagued with severe insolubilities. Other approaches have used solution-phase syntheses to install oligothiophene units. Schillinger, E. K., *Adv. Mater.* 21:1562 (2009); Stone, D. A., *Soft Matter* 5:1990 (2009).

The presently disclosed subject matter demonstrates how small peptide sequences with π-conjugated oligomers directly embedded in the peptide backbone promote assembly into one dimensional (1-D) nanostructures with strong π-π intermolecular electronic communication under completely aqueous and physiologically relevant conditions. The presently disclosed methods provide for the presentation of bioactive small peptides and other molecular recognition elements on the periphery of the nanostructure. The presently disclosed synthetic approaches are fundamentally different from covalent modification of preformed nanostructures or single proteins in that the peptidic structure encourages or enforces the formation of π-stacked conduits within the assembled objects. See Wang, Q., et al., *Angew. Chem., Int. Ed.* 41:459-462 (2002); Kas, O. Y., et al., *Chem. Mater.* 18:4238-4245 (2006).

Synthetic biomaterials whose properties can be regulated by external stimuli offer useful scaffolds for cell adhesion and growth. See Lahann, J., et al., *Science* 299:371-374 (2003); Langer, R. *MRS Bull.* 31:477-485 (2006). Biological architectures that incorporate π-conjugated materials are attracting substantial attention in this regard, see Klok, H. A., et al., *Org. Biomol. Chem.* 2:3541-3544 (2004); Kong, X., and Jenekhe, S. A., *Macromolecules* 37:8180-8183 (2004); Ashkenasy, N., et al., *Small* 2:99-102 (2006), as evidenced in polypyrrole-based cell scaffolds and artificial muscles. See Schmidt, C. E., et al., *Proc. Natl. Acad. Sci. U.S.A.* 94:8948-8953 (1997); Wallace, G., and Spinks, G. *Soft Matter* 3:665-671 (2007).

External stimuli also can provoke the assembly of biomolecular components into functional nanostructures. These strategies are supported by the formation of β-amyloid plaques, where misfolded soluble proteins undergo hierarchical assembly to yield fibrils having a diameter ranging from about 10 nm to about 50 nm with lengths of several micrometers. A wide diversity of small peptides form amyloid fibrils, and substantial research efforts seek to describe their formation, see Lashuel, H. A., et al., *J. Am. Chem. Soc.* 122:5262-5277 (2000); MacPhee, C. E., and Dobson, C. M., *J. Am. Chem. Soc.* 122:12707-12713 (2000), prevent their formation, and even use the process for advanced materials. See, for example, Zhang, S. G., et al., *Proc. Nat. Acad. Sci. U.S.A.* 90:3334-3338 (1993); Collier, J. H., and Messersmith, P. B., *Adv. Mater.* 16:907-910 (2004); Haines, L. A., et al., *J. Am. Chem. Soc.* 2005 127:17025-17029 (2005); Smeenk, J. M., et al., *Angew. Chem., Int. Ed.* 44:1968-1971 (2005); Davies, R. P. W., et al., *Supramol. Chem.* 18:435-443 (2006).

Provided herein are two general methods for embedding a π-conjugated unit within the backbones of self-assembling peptides, wherein each method presents subtle, but important, differences with respect to the direction of their N-to-C termini extending from the central π-electron linker.

II. One Dimensional Optoelectronic Nanostructures Derived from the Aqueous Self-Assembly of π-Conjugated Oligopeptides Constructed Through the Use of π-Conjugated "Amino Acids"

In some embodiments, the presently disclosed subject matter provides a method for constructing well-defined 1-D nanostructures with biologically responsive and electronically useful properties from molecular precursors. To harness this process to control π-π interactions, the π-system must be embedded directly into the peptide backbone. One approach disclosed herein includes synthesizing bioelectronic peptide molecules through designing π-conjugated units that have at opposite ends of the molecule a free carboxylic acid and a Fmoc-protected amino acid. This particular embodiment provides a method for embedding a π-conjugated unit within the backbones of self-assembling peptides having, in representative, non-limiting embodiments, the following N-to-C polarity:

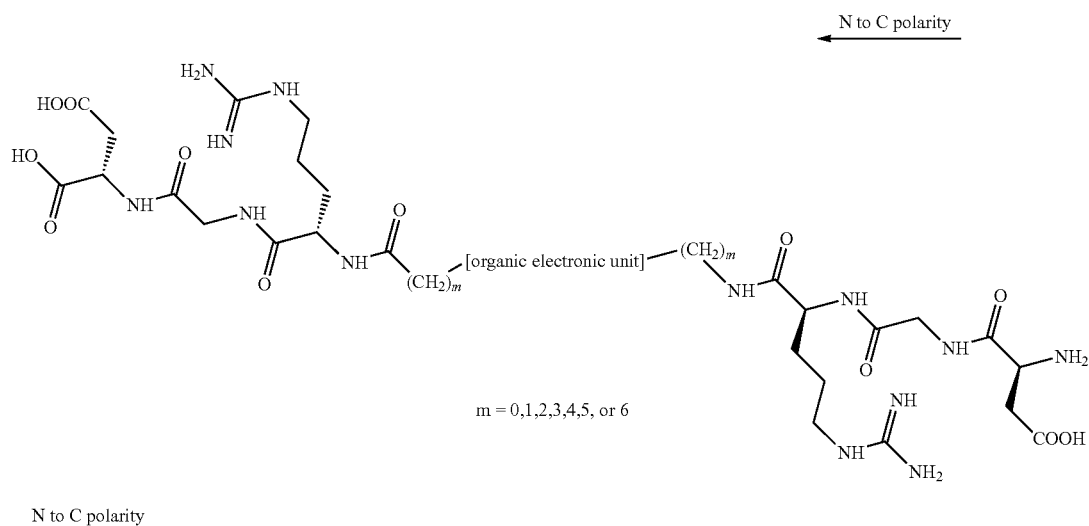

m = 0,1,2,3,4,5, or 6

More particularly, referring now to Scheme 1 and FIG. 3, in an exemplary, non-limiting method for preparing the presently disclosed π-conjugated oligopeptides, bithiophene 1 bearing a fluorenylmethyl-oxycarbonyl (Fmoc)-protected amine and a free carboxylic acid was prepared.

With compound 2, environmental conditions that promoted carboxylate charge screening (e.g., HCl or $CaCl_2$) initiated self-assembly, which resulted in the macroscopic formation of self-supporting gels suggestive of entangled 1-D structures. For example, the IR spectrum of compound 2

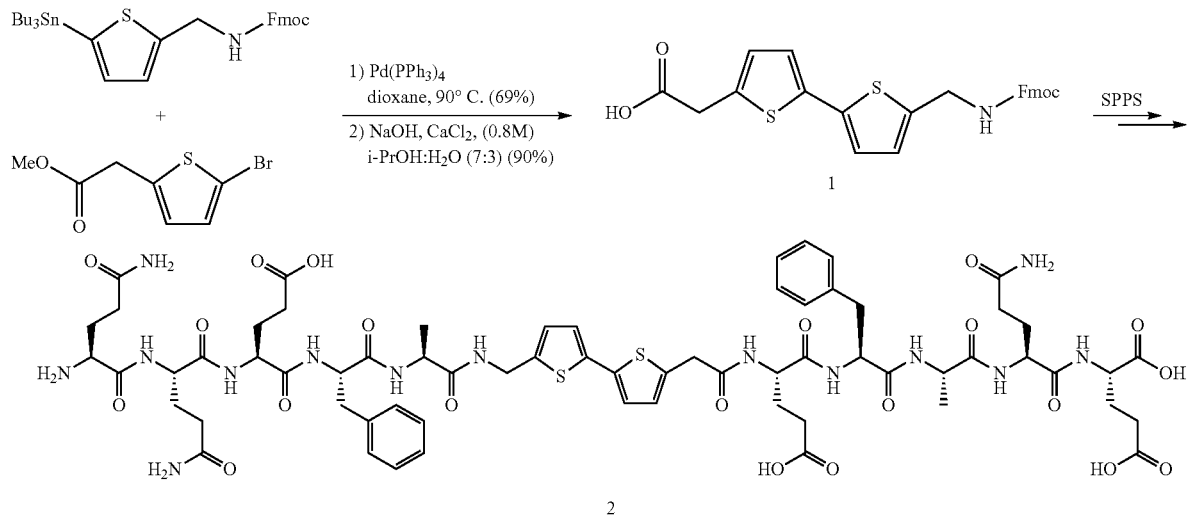

Scheme 1. Construction of Bithiophene Fmoc-Amino Acid 1 Used to Construct Self-Assembling Peptides, Such As Compound 2.

Bithiophene 1 represents the shortest member of the oligothiophene class of p-channel organic semiconductors and mimics amino acid building blocks commonly employed in solid-phase peptide synthesis (SPPS). Referring once again to Scheme 1, this approach enables direct incorporation of bithiophene into the backbones of known β-sheet forming motifs to yield molecules, such as compound 2, as confirmed by mass spectral analysis (see FIGS. 6A and 6B). See Davies, R. P. W., et al., *Supramol. Chem.* 18:435-443 (2006). Previously, complex nonsymmetric π-systems have been embedded within soluble biological motifs. See Wang, W., et al., *J. Am. Chem. Soc.* 125:5248-5249 (2003); Gothard, C. M., et al., *J. Am. Chem. Soc.* 129:7272-7273 (2007).

displayed characteristic β-sheet amide I bands at 1630 $cm^{-1}$ and 1641 $cm^{-1}$ accompanied by minor random-coil contributions. See FIG. 5. The circular dichroism (CD) spectrum of freely soluble compound 2 showed no meaningful absorption, whereas the CD spectrum of assembled compound 2 had intense absorptions only associated with the π-conjugated unit (see FIG. 1A). Molecularly dissolved compound 2 exhibited a low-energy absorption $\lambda_{max}$ at 320 nm. (see FIG. 4). Excitation at 320 nm triggered strong photoluminescence at 380 nm (see FIG. 1B). Upon assembly, the absorption profile remained comparable, but the emission was dramatically quenched.

The bisignate CD response crossing over at 320 nm (coincident with the absorption $\lambda_{max}$) is a classic signature for exciton-coupled chromophores in chiral environments. Although formal H-aggregates require blue-shifted absorptions, the lower oscillator strength of compound 2 might have led to less-pronounced effects. The natural propensities for β-sheets to adopt macromolecular twists also would dictate twisted H-aggregates. See Cornil, J., et al., *J. Am. Chem. Soc.* 120:1289-1299 (1998); Schenning, A., et al., *J. Am. Chem. Soc.* 123:409-416 (2001).

Although X-ray diffraction was inconclusive, the photophysics associated with the spectroscopic behavior disclosed immediately hereinabove indicates that the presently disclosed bithiophene π-systems intimately associate within a twisted chiral environment imposed by β-sheet interactions throughout the assembled structure.

A representative TEM image of compound 2 on formvar/carbon coated grids showing the formation of 1-D nanostructures is provided in FIG. 10. Further, atomic force microscopy (AFM) of gel samples deposited on mica revealed one-dimensional (1-D) nanostructures having heights ranging from about 2 nm to about 6 nm (FIGS. 1C and 1D; see also FIGS. 7-9). Given that compound 2 is approximately 42 Å in length, these structures are consistent with coiled tape-like or even more complex fibrillar structures, early thermodynamic sinks on the assembly energy landscape that spans from free molecule to large amyloid-like fiber. The rigidity of these structures is evident in the larger height profiles near crossover junctions. In some cases, 1-D structures resting over a monolayer of flat tapes passivating the mica surface (approximately 1 nm in height) were resolved; an observation that can be attributed to strong interactions between flat tapes and the highly polar mica surface. See Whitehouse, C., et al., *Angew. Chem., Int. Ed.* 44:1965-1968 (2005). Without wishing to be bound to any one particular theory, the influence of the backbone-embedded quadrupole moment of the π-cloud likely plays a role in affecting peptide-surface interactions: nanostructures deposited on nonpolar substrates did not show any evidence for monolayer passivation.

The presently disclosed model (see FIG. 2) starts with the formation of β-sheets yielding twisted ribbon 1-D structures (akin to telephone cords) with the same handedness as natural β-sheets. The more favorable antiparallel configuration shown at left (FIG. 2) is thought to occur, but this configuration cannot unambiguously be determined from the presently disclosed data. These structures can adsorb directly on the surface or they can aggregate with other tapes into larger fibrils, for example, as do other synthetic amyloid peptides. Regardless, the directionality of the hydrogen-bonding network coincides with the π-stacking axis with a calculated intermolecular π-π distance of approximately 5 Å. This relatively long distance still enables electronic communication as described hereinabove and as witnessed by energy transfer among isolated chromophores within α-helical and β-sheet peptides. See Kas, O. Y., et al., *J. Am. Chem. Soc.* 126:336-343 (2004); Kayser, V., *J. Am. Chem. Soc.* 126:336-343 (2004).

Referring now to FIG. 1D and FIG. 9, the AFM images reveal superstructural undulations with periodicities of approximately 76 nm as found in the right- and left-handed helical superstructures within natural amyloid sequences. See Mesquida, P., et al., *J. Mater. Sci. Mater. Med.* 18:1325-1331 (2007); Rubin, N., et al., *J. Am. Chem. Soc.* 130:4602-4603 (2008). Prospects for "molecular torque" caused by competing thermodynamic preferences to maximize β-sheet hydrogen bonding and minimize electrostatic repulsion among the bithiophene π-clouds also is acknowledged. See Li, L. S., et al., *Angew. Chem., Int. Ed.* 46:5873-5876 (2007).

Representative procedures for preparing and characterizing such materials are provided hereinbelow in Example 1.

III. On-Resin Dimerization Incorporates a Diverse Array of π-Conjugated Functionality within Aqueous Self-Assembling Peptide Backbones In typical solid-phase peptide synthesis protocols, it is assumed that the reactive amine terminus exposed at the end of the immobilized peptide will react with the activated carboxylic acid of the incoming residue. Because the amine terminus of the incoming residue is protected, undesired polymerization does not occur and any residues that have reacted with the resin-bound peptide are effectively "endcapped" until a later synthetic step removes the protecting group and exposes a new amine ready for continued elongation.

This general synthesis strategy was employed in the approach for synthesizing bioelectronic peptide molecules through designing π-conjugated units that had at opposite ends of the molecule a free carboxylic acid and a Fmoc-protected amino acid, as disclosed hereinabove. This unit served as a chain extender similar in execution to a typical Fmoc-protected amino acid. This approach required, however, complex synthetic chemistry to prepare the requisite π-conjugated "amino acids" in sufficient material quantities to be useful for solid phase peptide syntheses on scales that would provide reasonable amounts of materials, e.g., approximately hundreds of milligrams of material.

In contrast, in some embodiments, the presently disclosed subject matter provides a route to π-conjugated units that can be flanked by peptide segments that capitalizes on an on-resin dimerization mode of reactivity. By presenting an immobilized peptide bearing deprotected free amines with a difunctional diacid or dianhydride chain extender, double imidation or amidation among two of the immobilized peptides can be achieved. Cleavage of this symmetric dimer then leads to a similar peptide[π-conjugated unit]-peptide construct.

Further, the synthetic chemistry to prepare the symmetric diacids for this approach is more scaleable and straightforward and representative materials for incorporating the π-conjugated unit into the peptide backbone, e.g., naphthalene dianhydrides and perylene dianhydrides, are readily available. Representative procedures for these on-resin dimerizations are disclosed herein below and, more particularly, in Example 2.

Accordingly, in some embodiments, disclosed herein are methods for the rapid and efficient solid-phase incorporation of several prototypical (and easily prepared) organic semiconductors and fluorescent chromophores into the backbones of oligopeptides that undergo supramolecular polymerization into sub-10 nm one-dimensional (1-D) nanostructures capable of fostering electronic delocalization in completely aqueous environments. These electronic structures fall in a size regime not available through bottom-up molecular synthesis or via conjugated polymer nanolithography. Further, the presently disclosed nanostructures mimic, in part, the structural elements of the extracellullar matrix.

More particularly, in some embodiments, the presently disclosed subject matter demonstrates that π-conjugated dianhydrides and π-conjugated dicarboxylic acids are viable cross-linking agents between resin-immobilized peptide sequences generated through fluorenylmethyl-oxycarbonyl (Fmoc) solid-phase peptide synthesis (SPPS). See, for example, FIG. 11, which is a schematic representation of the presently disclosed on-resin cross-linking of immobilized peptide chains via amidation or imidation of π-conjugated dielectrophiles.

In representative embodiments, the N-terminal Fmoc-protecting groups can be removed, and the resin can be treated with a π-conjugated electrophile under suitable activation conditions to effect double amidation (or imidation) crosslinks. Cleavage of the peptide from the solid support yielded the π-electron unit, e.g., an organic electronic unit as defined herein, flanked by two peptide sequences. This site-site reactivity is not unusual for diacid crosslinkers, Farrall, M. J., and Frechet, J. M. J., *J. Am. Chem. Soc.* 100:7998 (1978); Rovero, P., et al., *Lett. Pept. Sci.* 2:27 (1995); Ladame, S., *Org. Lett.*, 4:2509 (2002); Biernat, M., *Bioconjugate Chem.* 17:1116 (2006), but it has been exploited for soluble molecular entities rather than for self-assembling materials.

The sequence resulting from the presently disclosed dimerization process presents N-to-C peptide polarity extending outward from the conjugated center leaving the molecule with two carboxylic acid termini. Accordingly, this particular embodiment provides a method for embedding a π-conjugated unit within the backbones of self-assembling peptides having, in representative, non-limiting embodiments, the following N-to-C polarity:

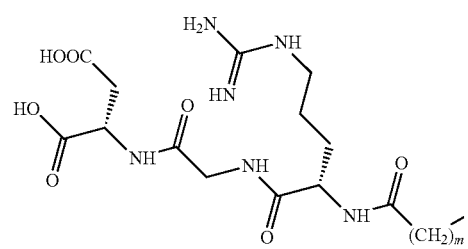
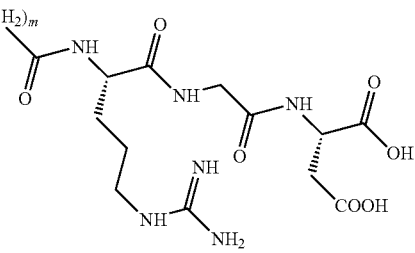

$m = 0, 1, 2, 3, 4, 5,$ or $6$

N to C polarity

The presently disclosed complex peptide molecules are, in some embodiments, derived directly from commercially available materials, including the SPPS resins and amino acids and the dianhydride chromophores. More particularly, the presently disclosed subject matter provides the scope of this on-resin dimerization for imparting π-electron function and discloses the initial spectroscopic and morphological characterization of the resulting nanomaterials. In exemplary embodiments, commercially available naphthalene (NDA) and perylene (PDA) dianhydrides underwent double imidation leading to rylene diimide peptides NDI 1 and PDI 2, respectively (see, e.g., FIG. 12).

Diimides are established n-channel semiconductors and robust dyes for light harvesting. Würthner, F., *Chem. Commun.* 1564 (2004); Cotlet, M., *J. Am. Chem. Soc.* 127:9760 (2005). In such embodiments, the imidation dimerization was optimal in a two-stage coupling protocol, whereby the resin-bound terminal amine was refluxed in pyridine, for example, for 10 hours with 0.3 equivalents of the dianhydride followed by the addition of 0.2 equivalents more. After 10 hours, the resin was rinsed and subjected to a "blank" reflux cycle in pyridine to drive maximal imide bond formation. The dimerized peptides and unreacted peptide fragments were the dominant compounds observed in the crude material isolated after resin cleavage with only trace amounts of mono-imidated products bearing anhydride termini (resulting from incomplete dimerization). Referring once again to FIG. 12, simple triturations with ether and acetonitrile provided purified peptide 1 and peptide 2 in modest yields.

In other representative embodiments, a series of π-conjugated diacids were examined as amidation partners, thus yielding peptides bearing other common π-electron units of contemporary materials interest, such as oligothiophenes (OTs, 3 and 4), oligophenylenes (OPs, 5) and oligophenylene vinylenes (OPVs, 6) as also provided in FIG. 12. In certain embodiments, representative oligothiophene (OT) diacids with intervening methylene spacers between the thiophenes and the carboxylic acids gave inferior results. For example, intense and unusual color changes were observed during SPPS, suggesting inefficient diacid activation perhaps due to enhanced acidity of methylene protons.

These dimerizations proceeded best under standard Fmoc SPPS conditions by adding the diacid linker in two portions to react over 12-hour periods (0.3 and then 0.2 equivalents). These peptides survived the acidic cleavage conditions necessary for resin cleavage, but resins requiring less aggressive measures could be used for sensitive chromophores. The presently disclosed diacids were limited to those readily available from known precursors: for example, OT-3 was prepared through lithiation of terthiophene followed by treatment with dry ice. See, Ni, Z., et al., *J. Am. Chem. Soc.* 127:12752 (2005). One of skill in the art, however, would recognize that other π-conjugated diacids would be suitable for use with the presently disclosed subject matter.

This reactivity was not limited to N-terminal glycine residues: for example, referring once again to FIG. 12, N-terminal alanine and phenylalanine resins provided comparable degrees of dimerization leading to peptide 7 and peptide 8. In these exemplary embodiments, the sequences were purposefully kept small and comprised residues known to bias β-sheet formation (e.g., Val, Phe). The isolated yields for the dimerizations were modest (30-45%), and could not be driven to greater completion despite numerous variations in stoichiometries and activation protocols. The Wang resins commercially available for peptide synthesis, however, usually have low loadings to minimize peptide aggregation and side-site chemistry, and yields should increase with dense resin loading. The modest yields are justifiable in light of the commercial availability of the dianhydrides, the much more facile syntheses of the requisite diacids of longer π-electron units, and the ability to do all peptide synthetic manipulations on the solid-phase.

Several approaches exist to create nanomaterials via the assembly of π-electron units in organic solvents, but general design strategies to do so in aqueous (and physiologically relevant) environments are not as well established. The presently disclosed self-assembly methods do not require an organic solvent. Said another way, the presently disclosed peptide-[organic electronic unit]-peptide materials can undergo self assembly in the absence of, or essentially in the absence of, an organic solvent. Despite the dramatic differences among the embedded quadrupoles, all peptides described herein underwent self-assembly. Maintaining high degrees of intermolecular π-electron communication in aqueous media within supramolecular 1-D aggregates built from these peptides requires parallel β-sheets among the peptide backbones, Levin, S, and Nowick, J. S., *J. Am. Chem. Soc.* 129:13043 (2007); Freire, F. and Gellman, S. H., *J. Am. Chem. Soc.*, 131:7970 (2009). The presently disclosed compounds revealed characteristic amide-I IR stretches between 1630-1640 cm$^{-1}$.

The peptides disclosed herein were designed to be molecularly dispersed at basic pH (specifically, at pH levels above aspartic acid's pK$_a$) due to the electrostatic repulsion among the deprotonated carboxylic acids. Lowering the solution pH protonated the carboxylates, thereby screening the charges among the peptides and allowing other favorable enthalpic interactions to guide the assembly process. As common for many self-assembling peptides, see Aggeli, A., et al., *Nature*, 386:259 (1997); Qu, Y., et al., *J. Am. Chem. Soc.* 122:5014 (2000); Hartgerink, J. D., et al., *Science* 294:1684 (2001); Pochan, D. J., *J. Am. Chem. Soc.* 125:11802 (2003); Collier, J. H., and Messersmith, P. B., *Adv. Mater.*, 16:907 (2004), this process was accompanied by the formation of self-supporting hydrogels from solutions with very low peptide weight percents (0.1-0.5 wt %, FIGS. 13b-d).

Atomic force microscopy (AFM) revealed that the internal structures of the formed hydrogels consisted of flat tape 1-D nanostructures that were approximately 2 nm in height (see FIGS. 13e and 13f. Larger and more hierarchically ordered objects were not observed, indicating that the energetics of the presently disclosed process present sufficient barriers to arrest the assembly at early stages of complexity. See Lashuel, H. A., et al., *J. Am. Chem. Soc.*, 122:5262 (2000); Aggeli, A., et al., *Proc. Nat. Acad. Sci. USA* 98:11857 (2001).

Figure 14:
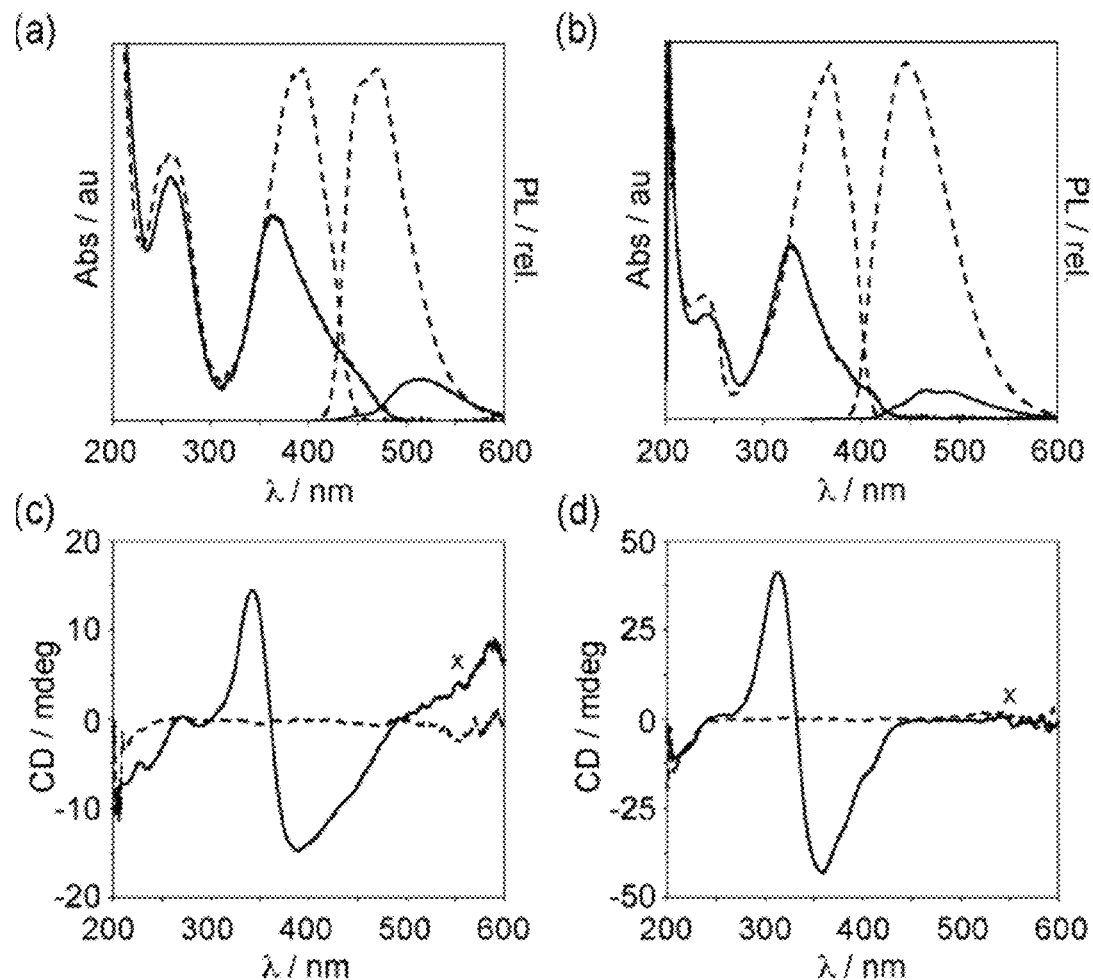

Steady-state absorption and photoluminescence (PL) data showed the classic absorption blue-shifts and PL quenching and red-shifts expected upon the formation of H-like aggregates of the OT and OPV peptides in acidic aqueous conditions (see FIGS. 14a and FIG. 14b). See Kasha, M., et al., *Pure Appl. Chem.* 11:371 (1965).

Material that was purified via simple trituration and via HPLC gave self-consistent spectral trends. The measurements at acidic pH were conducted on spectroscopic solutions of aggregates (generated by acidifying dilute solutions of soluble peptides) rather than on bulk hydrogels, but these photophysical changes were markedly visible macroscopically (see FIGS. 13b-d). Similarly, circular dichroism (CD) at basic pH led to little or no absorbance in the low-energy visible region, but acidic solutions showed very strong and characteristic bisignate Cotton effects indicative of chromophore interactions within helical or otherwise chiral environments (FIGS. 14c and 14d). These data reveal the substantial electronic delocalization existing within the peptidic nanostructures.

IV. Representative Embodiments

Accordingly, the presently disclosed subject matter provides general and efficient methods of preparing new classes of peptides bearing internal π-conjugated segments that can be manipulated and assembled into 1-D nanostructures in completely aqueous and physiologically relevant environments. More particularly, the presently disclosed subject matter provides a composition comprising one or more π-conjugated oligopeptides having a structure: peptide-[(organic electronic unit)-peptide]$_n$, wherein n is an integer from 1 to 10; the organic electronic unit is selected from the group consisting of an electroactive material, a chromophore, a fluorescent material, and/or a material having an environmentally sensitive optoelectronic property; and each peptide can be the same or different and comprises from 2 to 100 naturally occurring amino acid residues or a variant thereof. In some embodiments, n is selected from the group consisting of 1, 2 or 3. In particular embodiments, n is 1.

As used herein, the term "organic electronic unit" is used interchangeably with the terms "π-conjugated segment," "π-conjugated oligomer," and "π-conjugated unit" and is intended to mean a molecule, a portion of a molecule or a chemical moiety comprising one or more conjugated linkages of arenes, heteroarenes, and other unsaturated groups, such alkenes, alkynes, and the like, having delocalized π-electron properties as will be understood by those of skill in the art.

As used herein, the term "arene" includes monocyclic and polycyclic aromatic hydrocarbons. Representative arenes include benzene and substituted benzenes, biphenylene, and substituted biphenylenes. Representative polycyclic aromatic hydrocarbons include naphthalene, acenaphthylene, acenaphthene, fluorene, phenanthrene, anthracene, fluoranthene, pyrene, perylene, benz[a]anthracene, chrysene, benzo[b]fluoranthene, benzo[k]fluoranthene, benzo[a]pyrene, dibenz[a,h]anthracene, benzo[g,h,i]perylene, and indeno[1,2,3-cd]pyrene.

As used herein the term "heteroarene" includes heterocyclic compounds derived from arenes by replacement of one or more methine (—C≡) and/or vinylene (—CH═CH—) groups by trivalent or divalent heteroatoms, e.g., oxygen, nitrogen, and sulfur, respectively, in such a way as to maintain the π-electron system characteristic of aromatic systems. Thiophene is an example of a heteroarene.

Alkenes include acyclic branched or unbranched hydrocarbons having at least one carbon-carbon double bond and the general formula $C_nH_{2n}$.

Alkynes include acyclic branched or unbranched hydrocarbons having a carbon-carbon triple bond and the general formula $C_nH_{2n-2}$, RC≡CR.

As used herein, an "oligomer" includes a few monomer units, for example, in contrast to a polymer that potentially can comprise an unlimited number of monomers. Dimers, trimers, and tetramers are non-limiting examples of oligomers.

The organic electronic units can be varied, for example, to include fluorescent materials, electroactive materials, and/or materials that might have environmentally sensitive optoelectronic properties. Such organic electronic units include, for example, the α-oligothiophenes (bithiophene, terthiophene, quaterthiophene, and the like, and diacids thereof) used for p-channel (hole-transporting) organic semiconductors, oligophenylenes and diacids thereof, the rylene diimides (naphthalene and perylene diimides, and the like) used for dyestuffs and for n-channel (electron-transporting) organic semiconductors, and the oligo(p-phenylene vinylenes and diacids thereof) used as intense fluorophores for light emission and as dyes for photovoltaics. Other suitable examples of organic electronic units will be evident to those of skill in the art.

As used herein, the term "peptide segment" is intended to mean in some embodiments a peptide of 2 to 100 amino acid residues, including any integer from 2 to 100, and in some embodiments, 2 to 15 amino acid residues, including 2, 3, 4, 5, 6, 7, 8, 9, 10, 11, 12, 13, 14, and 15 amino acid residues, which are obtainable by standard peptide synthesis protocols known in the art.

As used herein, an "amino acid residue" is a residue of a naturally occurring amino acid or a variant thereof, including but not limited to alanine, arginine, asparagine, aspartate, cysteine, glutamate, glutamine, glycine, histidine, isoleucine, leucine, lysine, methionine, phenylalanine, proline, serine, threonine, tryptophan, tyrosine, valine, 5-hydroxylysine, 4-hydroxyproline, thyroxine, 3-methylhistidine, ε-N-methyllysine, ε-N,N,N-trimethyllysine, aminoadipic acid, γ-carboxyglutamic acid, phosphoserine, phosphothreonine, phosphotyrosine, N-methylarginine, and N-acetyllysine. Naturally occurring amino acid residues are preferred.

In addition to naturally occurring amino acids and variants thereof, other residues that are compatible with standard solid-phase peptide synthesis protocols can be used to form the compounds described herein, as will be appreciated by those of skill in the art. Representative residues include, but are not limited to, moieties such as β-amino acids and longer chain amino alkanoic acids, peptide nucleic acids, and amino benzoic acids.

Peptide segments can be varied, for example, to encourage specific cellular adhesion through integrin mediated binding (RGD tripeptide as fibronectin mimic, IKVAV (SEQ ID NO:6) as a laminin mimic, and the like) or to encourage other molecular recognition events (carboxylates to sequester metal ions, defined entities of a natural or unnatural origin to promote a chemical interaction).

It is contemplated that the presently disclosed π-conjugated oligopeptides can include multiple units, for example, peptide-(organic electronic unit)-peptide-(organic electronic unit)-peptide, and the like, wherein the π-conjugated amino acid is added to the growing peptide, followed by additional peptide coupling, followed by a new π-conjugated amino acid, followed by a new peptide sequence, and the like, wherein the "peptide" includes any amino acid residue as defined hereinabove suitable for use with solid-phase synthesis.

As disclosed hereinabove, in some embodiments, self assembly of the presently disclosed π-conjugated oligopeptides can be initiated by acidic pH or $Ca^{2+}$ ions, i.e., environmental conditions that promote carboxylate charge screening. In other embodiments, depending on the choice of peptides that make up the molecule, self assembly can be initiated under basic pH or in the presence of other metal ions. For example, in embodiments wherein the peptide comprises lysine residues, the molecules would be soluble at acidic pH due to amine protonation and then triggered to undergo self assembly through ammonium neutralization at neutral or more basic pH.

Notably, the presently disclosed methods for preparing peptide-[organic electronic unit]-peptide nanostructures do not require the presence of additional moieties to render the presently disclosed compounds soluble, such as oligo(ethylene oxide)s, which are known in many circumstances to resist specific biological adhesion. The photophysical changes observed upon assembly demonstrate the strong electronic communication existing within the amyloid-like aggregates as mediated by π-stacking among molecular components, a critical component necessary for charge transport or exciton delocalization in nanostructures with semiconductive π-systems. Accordingly, in some embodiments, the presently disclosed subject matter provides methods for engineering biologically relevant and electronically functional one-dimensional nanostructures comprising π-conjugated amino acids, including bioactive peptide sequences.

Further, the aqueous nature of the assembly process described herein provides a unique way to subject biologically relevant π-electron materials to exciton coupling as imposed by the peptide hydrogen-bonding network established within 1-D nanostructures at size scales unavailable for soft electronic materials without using toxic organic solvents. The presently disclosed synthesis strategies will enable more detailed photophysical studies to understand the energy migration possible within nanostructures containing tunable electronic conduits now that the embedded π-electron group can be varied in such a rapid and systematic manner, thereby assisting with their transition into imaging and bioelectronics applications.

The potential to use environmentally-sensitive π-electron dyes as reporter groups for the folding or assembly processes of amyloid-like materials will add sophistication to the characterization of the internal structure of self-assembled biomaterials as a complement to IR and CD spectroscopies that are not entirely reliable for non-natural peptide assemblies. Venyaminov, S. Y., *Anal. Biochem.* 198:250 (1991); Surewicz, W. K., *Biochem.* 32:389 (1993).

V. Biosensing and Biological Adhesion Applications

As disclosed hereinabove, the presently disclosed subject matter provides a strategy to impart water solubility to π-conjugated organic electronic units and methods to provoke the assembly of these molecules into defined one-dimensional nanostructures Thus, in one embodiment, the presently disclosed subject matter provides a solution to the severe aqueous insolubilities associated with the hydrophobic π-conjugated organic electronic materials, and at the same time, offers a method to assemble the structures in aqueous environments. The peptidic nature of the presently disclosed molecules allows for an easy transition into biological environments and the ability to fine tune specific biorecognition events as governed by the initial peptide sequence chosen prior to synthesis. The merging of electronic material and biological adhesive material can lead to materials for use in, for example, tissue repair and sensing applications.

In particular embodiments described herein, π-conjugated organic electronic units have been rendered water soluble, yet at the same time, the ionizable residues of the peptide allow for the solubility to be altered through the addition of exogenous agents, such as acid or physiologically relevant concentrations of calcium ions. The methods described herein allow for π-conjugated systems to be processed from aqueous media (and physiologically relevant media) into functional nanostructures that are directly relevant to cell proliferation and sensing schemes.

Thus, in one aspect, the presently described compounds and methods comprise, e.g., peptide segments interlinked with π-conjugated segments having improved solubility and nontoxicity compared to previously known compounds and methods. Further, the individual components offer the option of being co-mixed and co-assembled, thereby bringing the specific molecular properties of the components in mixture together in the aggregate.

In one embodiment, upon assembly, the π-conjugated units are placed in close proximity such that useful electronic conduits are established. By "electronic conduit" is meant, for example, a structure that is capable of transmitting an optical or electrical signal. The photophysical effects of the assembly function as elements of energy transfer schemes in biological environments, and perturbations of said effects can serve, for example, as the basis of biosensing schemes. The peptide segments of the self-assembling molecules described herein can be designed such that specific biological interactions can be crafted as preludes to employing these nanostructures as electroactive surrogates for structural proteins present in the extracellular matrix.

Further, by altering the peptide composition, compounds as described herein can be designed so as to adhere to components of extracellular space (ECS), target cardiac tissues (e.g., a small peptide that would allow cardiac cells to adhere and multiply), target spinal cord (e.g., injected in a solution of the starting compounds that would spontaneously assemble on the spot). In addition, these compositions could be used to control the fate of differentiating cells, such as stem cells and progenitor cells.

The presently disclosed compounds also can be fashioned ex vivo and implanted, used in hydrogels for encapsulating cells, or as aligned arrays with electronic functionality. Once assembled or implanted in vivo, it is expected that, in certain embodiments, these compounds will be able to be polarized beyond known prior compositions. For example, an external electric bias or electronic field could be applied to alter ionic properties, externally change wettability, or turn on or off particular cellular interactions, e.g., through polarization or electric signaling.

Accordingly, in specific embodiments, the compounds can be assembled into sensor arrays for detection of biological interaction, 3-D hydrogel scaffolds for tissue regeneration, aligned arrays to control or guide the extension of cellular processes with implications for the establishment of artificial cell-cell communication networks. It is expected that optoelectronic properties also will allow use of the presently disclosed peptide-[organic electronic unit]-peptide compounds as imaging agents to visualize the direct incorporation of a labeled dye into the macromolecular architecture of forming amyloid deposits, and the like.

For these and other purposes, in some embodiments, the π-conjugated oligopeptides and nanostructures may be incorporated into medical devices, e.g. to be implanted into a subject. Such medical devices may optionally include other components, e.g., suitable housing, batteries, radio frequency tags and other device electronic components, and the like, necessary for particular functions to be carried out. By "implantable medical device" is meant a device or object having a therapeutic or diagnostic purpose that is suitable for implantation in the body of a subject (e.g., of size and composition to be physiologically acceptable, as determined by those of skill in the art).

By "subject" is meant an animal, in particular a mammal (e.g., a human or a laboratory animal) in which the presently disclosed peptide-[organic electronic unit]-peptide nanostructure(s) or medical devices comprising the same can be implanted for diagnostic, therapeutic or experimental purposes. More particularly, the "subject" is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The defined nanostructures may be formed ex vivo and inserted or implanted at a target site in the patient, e.g. by a catheterization, endoscopic or laparoscopic method, by surgery, by injection, and the like. By "defined nanostructure" is meant a structure comprising an ordered (nonrandom) assembly of π-conjugated segments in a functional orientation. Further, as used herein, the term "nanostructure," refers to a structure having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanostructure has at least one dimension, for example, a height, of about 1 nm to 10 nm.

Although the presently disclosed subject matter does not claim order in a crystallographic sense, the objects formed herein are sufficiently ordered to achieve electronic function within an observable, manipulatable and possibly isolable one-dimensional structure (meaning, two of the three spatial dimensions of the structure are under 10 nm in size). Optionally, additional components/agents, such as functional peptides, fluorescent moieties, and the like also can be present. Alternatively, they may be created in situ by introducing a mixture or admixture of the appropriate π-conjugated oligopeptides under conditions such that the nanostructure(s) assemble at the desired target site.

The target site may be a tissue in which it is desired to stimulate proliferation of cells, e.g. cardiac tissue, or establish a conduit for electrical signaling, e.g. spinal cord, a tissue in which it is desired to measure chemical or electrical activity through the use of a biological sensor, a tissue in which it is desired to regulate activity using an external source (e.g. use of an electromagnetic field, radio signal, and the like).

In yet other embodiments, it is contemplated that the presently disclosed nanostructures can be used as biosensors, whereby cell adhesion or other molecular recognition as mediated by the peptide sequences presented on the periphery leads to a local deformation. This deformation should transmit to the underlying stacked π-electron conduit, thus leading to an attenuation of the optical or electrical properties, such as a wavelength shift or intensity alteration of a fluorescence response due to the breakup of a chromophore aggregate into a molecular chromophore, or such as an alteration of device electrical properties, such as charge mobilities, due to the disruption of the order within the self-assembled nanostructure. Conformational changes that follow from biological binding events can be exerted over the lengths of about one (1)

nm (10 Å) well in the range to provide dramatic perturbation for inter-chromophore communication.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Self-Assembling Peptides Bearing Organic Electronic Functionality Constructed from Pi-Conjugated "Amino Acids"

General Considerations

Reactions were performed in flame-dried glassware under an atmosphere of nitrogen. Non-aqueous solvents were degassed by sparging with nitrogen for 15 minutes prior to use and THF was passed through columns of activated alumina. Tetrakis(triphenylphosphine)palladium (Pd(PPh$_3$)$_4$) was obtained from Strem Chemicals. Chemicals for solid phase peptide synthesis (N-Methylpyrrolidone (NMP), O-(Benzotriazol-1-yl)-N,N,N',N'-tetramethyluronium hexafluorophosphate (HBTU), Wang resin, Fmoc-Amino acids) were obtained from Advanced ChemTech. All other chemicals were supplied by Sigma-Aldrich or Fisher and used as received. $^1$H-NMR and $^{13}$C-NMR were obtained at 400 MHz and 100 MHz respectively using a Bruker Avance 400 MHz FT-NMR spectrometer. Chemical shifts are reported in parts per million relative to residual protio solvent [CDCl$_3$ δ: 7.26 ($^1$H) and 77.00 ppm ($^{13}$C), DMSO δ: 2.50 ($^1$H) and 40.0 ppm ($^{13}$C), D$_2$O δ: 4.79 ($^1$H)]. 2,2,5,5-tetramethyl-1-(thiophen-2-ylmethyl)-1,2,5-azadisilolidine (A) was prepared by slow addition of 1,2-bis(chlorodimethylsilyl)ethane to a stirring solution of 2-thiophene methylamine and triethylamine at 0° C. in CH$_2$Cl$_2$. Mugurama, H., et al., Synthesis and Characterization of α,α'-Bis(aminomethyl)oligothiophenes and Their Related Compounds," *J. Heterocyclic Chem.* 33(1):173-8 (1996).

UV/Vis and Fluorescence

UV-vis absorption spectra were recorded using a Varian Cary 50 Bio UV-Visible spectrophotometer. Solution fluorescence measurements were performed on an ISS K2 multifrequency phase fluorometer (equipped with an ILC Technology Illuminator power supply). A stock solution of peptide (10 mg/mL) was brought to pH 8 by incremental addition of 2 μL of 1M KOH then filtered with 0.45 μm syringe filters. An 11 μM-solution of peptide was prepared in both neutral deionized H$_2$O and concentrated HCl to obtain spectra for the non-aggregated and self-assembled system, respectively. Fluorescence data was collected using samples prepared for UV/Vis.

Circular Dichroism

Circular dichroism measurements were carried out at room temperature using a Jasco J-810 spectropolarimeter. A stock solution of peptide (5 mg/mL) was brought to pH 8 by incremental addition of 2 μL of 1M KOH then filtered with 0.45- μm syringe filters. 400 μL of a 3.4-mM solution was then added to a 2.00-mm cuvet to obtain a spectrum of the non-assembled system. A spectrum of the self-assembled system was obtained by adding 100 μL 1M HCl and allowing a self-supporting gel to form.

Atomic Force Microscopy

Samples were analyzed by magnetic tapping mode AFM on an Agilent Technologies PicoSPM LE using probes purchased from Micromasch (NSC18 Co/Cr). A stock solution of peptide (10 mg/mL) was brought to pH 8 by incremental addition of 2 μL of 1M KOH. The peptide solution was filtered through a 0.45-μm syringe filter. 190 μL of peptide solution at a concentration of 0.7 mM was made acidic by the addition of 10 μL of 1M HCl. It was immediately vortexed to mix and allowed to sit for 10 minutes to allow it to form a self-supporting gel. The gel was then diluted to 0.07 mM and thoroughly mixed by vortex. A 10 μL-aliquot was deposited onto a freshly cleaved mica substrate and allowed to dry for one hour prior to imaging.

Infrared Spectroscopy

Samples of peptide were dried under high vacuum and analyzed by attenuated total reflectance (ATR) on a Nexus 670 E.S.P. Fourier transform infrared (FT-IR) spectrometer.

Transmission Electron Microscopy

Samples were analyzed on a Philips EM 420 TEM. A stock solution of peptide (10 mg/mL) was brought to pH 8 by incremental addition of 2 μL of 1M KOH. The peptide solution was filtered through a 0.45-μm syringe filter. 190 μL of peptide solution at a concentration of 0.7 mM was made acidic by the addition of 10 μL of 1M HCl. It was immediately vortexed to mix and allowed to sit for 10 minutes to allow it to form a self-supporting gel. The gel was then diluted to 0.07 mM and thoroughly mixed by vortex. A formvar/carbon coated grid was floated on a 10-μL drop of peptide solution. The grid was then floated on water for 10 seconds, floated on 1% PTA for 1 min, and the excess PTA removed by a #50 hardened Whatman filter paper. Images were captured using a SIS Megaview III digital CCD, and figures assembled using Adobe Photoshop with only linear adjustments in brightness and contrast.

Synthetic Procedures

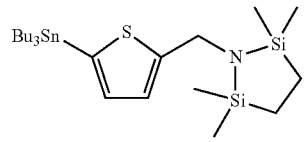

2,2,5,5-tetramethyl-1-(5-(tributylstannyl)thiophen-2-yl)methyl)-1,2,5-azadisilolidine (B)

Referring now to FIG. 3, a flame dried Schlenk flask under nitrogen was charged with a solution of STABASE-protected thiophene A (1.00 g, 3.91 mmol) in degassed THF (15 mL) and cooled to 0° C. While stirring, a solution of $^n$BuLi in hexanes (2.55 mL, 1.58 M, 4.03 mmol) was added dropwise and the reaction was stirred for 1 hour at 0° C. then allowed to warm to room temperature (RT). Bu$_3$SnCl (1.09 mL, 4.03 mmol) was then added at once and the reaction was stirred for an additional one hour. The reaction was diluted with ether and the organic phase was washed with brine and water, dried with magnesium sulfate, and concentrated by rotovap to yield the crude product as a yellow/orange oil, which was used without further purification (2.13 g, 3.91 mmol, crude). $^1$H NMR (CDCl$_3$) δ: 6.96 (m, 2H), 4.22 (s, 2H), 1.60-1.53 (m, 6H), 1.39-1.32 (m, 6H), 1.08-1.06 (m, 6H), 0.94-0.89 (m, 9H), 0.73 (s, 4H), 0.02 (s, 12H). $^{13}$C NMR (CDCl$_3$) δ: 154.0, 135.0, 134.7, 125.5, 40.8, 29.0, 27.3, 13.7, 10.8, 8.1, −0.4.

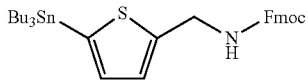

(9H-fluoren-9-yl)methyl (5-(tributylstannyl)
thiophen-2-yl)methylcarbamate (C)

Referring once again to FIG. 3, stannylated thiophene B (7.16 g, 13.1 mmol) was dissolved in EtOAc (33 mL) and stirred with 0.076M HCl (33 mL) for 30 minutes. The reaction was then added to a separation funnel, diluted with EtOAc, and the organic phase was washed with brine and water, dried with magnesium sulfate, and concentrated by rotovap. The resulting oil was taken up in 45 mL of a 1:1 THF:H$_2$O solution containing sodium bicarbonate (1.44 g, 17.1 mmol). Fmoc-OSu (4.44 g, 13.1 mmol) was then added portion wise over 30 minutes. The reaction was stirred for an additional three hours upon which it was diluted with water, acidified (pH=2-3) with 1M HCl, and extracted with EtOAc (3×). The organic phase was then washed with water, dried with magnesium sulfate, concentrated, and purified by chromatography on a plug of silica (5% EtOAc in hexanes) to yield the product as yellow oil (7.94 g, 12.7 mmol, 97%). $^1$H NMR (CDCl$_3$) δ: 7.80 (d, 2H, J=7.6 Hz), 7.63 (d, 2H, J=7.4 Hz), 7.42 (t, 2H, J=7.2 Hz), 7.33 (t, 2H, J=7.3 Hz), 7.12 (d, 1H, J=2.4 Hz), 7.06 (d, 2H, J=3.0 Hz), 5.29 (broad, 1H), 4.64 (d, 2H, J=5.8 Hz), 4.47 (d, 2H, J=7.0 Hz), 4.26 (t, 1H, J=6.9 Hz). $^{13}$C NMR (CDCl$_3$) δ: 171.2, 156.2, 146.7, 144.0, 141.4, 137.0, 135.4, 127.7, 127.2, 127.1, 125.1, 120.0, 66.9, 60.4, 47.3, 39.9, 29.0, 28.9, 27.3, 21.1, 14.3, 13.7, 13.7, 10.9.

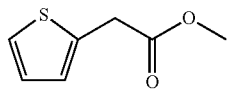

Methyl 2-(thiophen-2-yl)acetate

Thiophene acetic acid (27.3 g, 192 mmol) was treated with a solution of H$_2$SO$_4$ (5.76 mL, 108 mmol) in MeOH (384 mL) at reflux for one hour. The reaction was then cooled to room temperature, concentrated by rotovap, diluted with ether, washed with 5% sodium bicarbonate and brine. The organic phase was then dried with magnesium sulfate and concentrated by rotovap to yield the product as a yellow oil (27.4 g, 176 mmol, 91%), which was used without further purification. The product matches data for commercially available methyl 2-(thiophen-2-yl)acetate (CAS No. 19432-68-9).

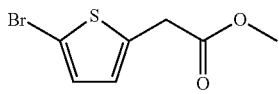

Methyl 2-(5-bromothiophen-2-yl)acetate (D)

Referring once again to FIG. 3, a solution of methyl 2-(thiophen-2-yl)acetate (27.44 g, 175.7 mmol) was dissolved in DMF (500 mL) and stirred in the dark as NBS (37.52 g, 210.8 mmol) was added portion wise. The reaction was stirred for three hours at which TLC indicated completion of the reaction. The reaction was diluted with ether and the organic phase was washed with ammonium chloride and water, then dried with magnesium sulfate and concentrated by rotovap. The resulting crude oil was purified by triturating with hexanes, decanting off the organic phase above the oil, then subjecting the oil to chromatography on a gradient plug of silica gel (hexanes to 10% EtOAc in hexanes) to yield the product as a yellow oil (33.90 g, 144.2 mmol, 82%). The product matches literature data. Kranich, R., et al., "Rational Design of Novel, Potent Small Molecule Pan-Selectin Antagonists," *J. Med. Chem.* 50:1101-1115 (2007). $^1$H NMR (CDCl$_3$) δ: 6.89 (d, J=4.0 Hz, 1H), 6.69 (dt, J=4.0 Hz, 1H), 3.76 (s, 2H), 3.72 (s, 3H).

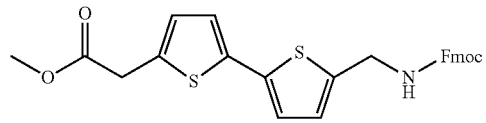

Methyl 2-(5'-((((9H-fluoren-9-yl)methoxy)carbony-
lamino)methyl)-2,2'-bithiophen-5-yl)acetate (E)

Referring once again to FIG. 3, a flame dried Schlenk flask was charged with Pd(PPh$_3$)$_4$ (0.220 g, 0.191 mmol), evacuated and placed under N$_2$. Degassed dioxane (21.0 mL) was cannulated in to a flame-dried round bottom flask containing stannylated and Fmoc-protected thiophene C (7.94 g, 12.7 mmol), which was dissolved and then cannulated into the Schlenk flask. Brominated thiophene methyl ester D (1.49 g, 6.36 mmol) was then added at once and the reaction heated to 90° C. and stirred for 18 hours. The reaction was cooled to room temperature, diluted with ether, and filtered through celite. The organic phase was then washed with brine and water, dried with magnesium sulfate, and concentrated by rotovap. The crude oil was taken into CH$_2$Cl$_2$ and purified on a plug of silica using CH$_2$Cl$_2$ as the mobile phase and the eluents were concentrated by rotovap. The resulting oil was triturated with hexanes and the solids that formed were filtered and rinsed with hexanes to yield the product as faint pink/tan solid (2.16 g, 4.41 mmol, 69%). $^1$H NMR (CDCl$_3$) δ: 7.76 (d, 2H, J=7.6 Hz), 7.59 (d, 2H, J=8.8 Hz), 7.39 (t, 2H, J=7.4 Hz), 7.30 (t, 2H, J=7.4 Hz), 6.96 (m, 2H), 6.82 (m, 2H), 5.17 (broad, 1H), 4.51 (d, 2H, J=5.9 Hz), 4.46 (d, 2H, J=7.1 Hz), 4.23 (t, 1H, J=6.7 Hz). $^{13}$C NMR (CDCl$_3$) δ: 170.6, 156.1, 143.8, 141.3, 140.2, 137.15, 137.0, 134.1, 127.7, 127.6, 127.0, 126.4, 125.0, 123.3, 123.2, 123.2, 123.1, 120.0, 66.8, 52.3, 47.2, 40.0, 35.4, 29.7. HRMS (FAB) m/z calculated for (C$_{27}$H$_{23}$NO$_4$S$_2$)$^+$ 489.1068. found 489.1069.

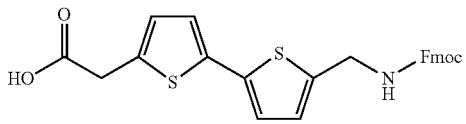

2-(5'-(((((9H-fluoren-9-yl)methoxy)carbonylamino)
methyl)-2,2'-bithiophen-5-yl)acetic acid (1)

Referring once again to FIG. 3, bithiophene amino ester E (2.16 g, 4.41 mmol) was dissolved in a 0.8 M CaCl$_2$ solution of $^i$PrOH:H$_2$O (7:3) (110 mL). The solution was then treated with NaOH (0.212 g, 5.29 mmol) and stirred for 18 hours at room temperature. The reaction was then heated to 40° C. and stirred for an additional six hours. The reaction was then neutralized with 1M HCl and diluted with EtOAc. The organic phase was then washed with water, dried with magnesium sulfate, and concentrated by rotovap. The crude oil was then dissolved in minimum amount of hot EtOAc and then precipitated by the addition of excess hexanes. The solids were filtered and rinsed with hexanes to provide the product isolated as tan solid (1.90 g, 4.00 mmol, 90%). $^1$H NMR (DMSO-d6) δ: 7.99 (t, 1H, J=5.9 Hz), 7.87 (d, 2H, J=7.4 Hz), 7.69 (d, 2H, J=7.4 Hz), 7.41 (t, 2H, J=7.6 Hz), 7.32 (t, 2H, J=7.4 Hz), 7.05 (d, 2H, J=3.4 Hz), 6.88 (d, 1H, J=3.8 Hz), 6.86 (d, 1H, J=3.4 Hz), 4.36 (d, 2H, J=7.0 Hz), 4.32 (d, 2H, J=5.7 Hz), 4.24 (t, 1H, J=6.8 Hz), 3.82 (s, 2H). $^{13}$C NMR (DMSO-d6) δ: 172.0, 156.6, 144.3, 142.5, 141.2, 136.3, 136.1, 136.0, 128.2, 128.1, 127.4, 126.6, 125.6, 123.4, 120.6, 65.9, 47.2, 35.5. HRMS (FAB) m/z calculated for $(C_{26}H_{21}NO_4S_2)^+$ 475.0912. found 475.0914.

General Synthesis of Peptides:

All peptides were synthesized using standard solid phase 9-fluorenyl-methoxycarbonyl (Fmoc) chemistry on a Wang resin preloaded with Fmoc-Glu (O-$^t$Bu). Fmoc deprotection was performed by mixing the resin in a piperidine/DMF (2:8) solution for 10 minutes (2×), then rinsing with DMF, MeOH, and DCM. For all standard amino acid couplings, 3.0 eq. (relative to the resin substitution) of Fmoc-protected amino acid was activated externally with 2.9 eq. of O-Benzotriazole-N,N,N',N'-tetramethyluronium hexafluorophosphate (HBTU) and 10 eq. of diisopropylethylamine (DIPEA). The activated Fmoc-protected amino acid was then added to a peptide chamber containing the Wang resin and mixed for three hours. The resin was then drained and rinsed with NMP, MeOH, and DCM then allowed to dry. All coupling and deprotection steps were monitored by performing a Kaiser test on a few resin beads which were removed from the peptide chamber after drying. The resin was prepared for cleavage by washing with acetic acid, DCM, and MeOH then drying under high vacuum. Cleavage from the resin and removal of side-chain protecting groups was accomplished by stirring the resin with 20 mL of trifluoroacetic acid (TFA), water, and triisopropylsilane (TIPS) (95:2.5:2.5) for three hours. The resin was removed by filtration and washed with 5 mL of the cleavage mixture. The filtrate volume was then reduced by half by rotovap and the peptide was precipitated by the addition of 200 mL cold diethyl ether. The precipitate was filtered and rinsed with cold diethyl ether to obtain the crude peptide. The crude peptide was then eluted off the filter with ammonium hydroxide, condensed by rotovap, and dried under high vacuum. The peptide was then triturated with acetonitrile and the solids filtered to yield the final product.

Compound 2.

For coupling of 1: 0.178 g (0.374 mmol) of 1 and 0.135 g (0.355 mmol) of HBTU was added to Wang-EQAFE-NH$_2$ and dissolved in 1:2 NMP:DCM, then 0.326 mL of DIPEA (1.87 mmol) was added and the reaction was mixed for 3 hours. Peptide 9 underwent two rounds of coupling to fully incorporate compound 1. Fmoc-deprotection, peptide elongation (A, F, E, Q, Q), and final cleavage from the resin was performed as described above. Final peptide was obtained as a brown powder. $^1$H NMR (D$_2$O) δ: 7.23-6.97 (m, 12H), 6.81 (broad, 1H), 6.76 (broad, 1H), 4.47 (broad, 2H), 4.37 (d, J=6.9 Hz, 2H), 4.21-3.91 (m, 10H), 3.62 (m, 2H), 2.98-2.72 (broad, 4H), 2.28-1.68 (broad, 29H), 1.24-1.16 (m, 6H). MS (ESI−) m/z calculated for $(C_{65}H_{82}N_{14}O_{21}S_2)^{2−}$/2: 729.79. found 729.55; m/z calculated for $(C_{65}H_{81}N_{14}O_{21}S_2)^{3−}$/3: 486.19. found 486.05.

Example 2

On-Resin Dimerization Incorporates a Diverse Array of Pi-Conjugated Functionality within Aqueous Self-Assembling Peptide Backbones General Considerations.

Reactions were performed in flame-dried glassware under an atmosphere of nitrogen. Non-aqueous solvents were degassed by sparging with nitrogen for 15 minutes prior to use and THF was distilled over sodium/benzophenone. Tetrakis(triphenylphosphine)palladium (Pd(PPh$_3$)$_4$) was obtained from Strem Chemicals. Chemicals for solid phase peptide synthesis (N-methylpyrrolidone (NMP), O-(benzotriazol-1-yl)-N,N,N',Ni-tetramethyluronium hexafluorophosphate (HBTU), benzotriazol-1-yl-oxytripyrrolidinophosphonium hexafluorophosphate (PyBOP), Wang resin, Fmoc-amino acids) were obtained from Advanced ChemTech. All other chemicals were supplied by Sigma-Aldrich or Fisher and used as received. $^1$H-NMR and $^{13}$C-NMR were obtained at 400 MHz and 100 MHz, respectively, using a Bruker Avance 400 MHz FT-NMR spectrometer, unless otherwise noted. Chemical shifts are reported in parts per million relative to residual protio solvent [CDCl$_3$ δ: 7.26 ($^1$H) and 77.16 ppm ($^{13}$C), d$_6$-DMSO δ: 2.50 ($^1$H) and 39.52 ppm ($^{13}$C), D$_2$O δ: 4.79 ($^1$H)].

General Synthesis of Peptides.

All peptides were synthesized using standard solid phase 9-fluorenylmethoxycarbonyl (Fmoc) chemistry on a Wang resin preloaded with the Fmoc-protected leading amino acid. Fmoc deprotection was performed by mixing the resin in a piperidine/DMF (2:8) solution for 10 minutes (2×), then rinsing with DMF, MeOH, and CH$_2$Cl$_2$. For all standard amino acid couplings, 3.0 eq. (relative to the resin substitution) of Fmoc-protected amino acid was activated externally with 2.9

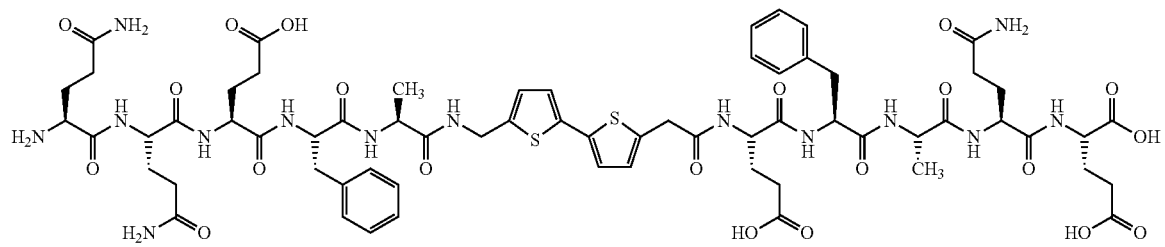

eq. of HBTU and 10 eq. of diisopropylethylamine (DIPEA) are dissolved in 10 mL of NMP. The activated Fmoc-protected amino acid was then added to a peptide chamber containing the Wang resin and mixed for three hours. The resin was then drained and rinsed with NMP, MeOH, and $CH_2Cl_2$ then allowed to dry.

All coupling and deprotection steps were monitored by performing a Kaiser test on a few resin beads which were removed from the peptide chamber after drying. Cleavage from the resin and removal of side-chain protecting groups was accomplished by stirring the resin with trifluoroacetic acid (TFA), water, and triisopropylsilane (TIPS) (95:2.5:2.5) for 3 hours (unless otherwise noted in individual peptide experimental). The resin was removed by filtration and washed with the cleavage mixture. The filtrate volume was then reduced on a rotary evaporator fitted with a KOH (aq) trap and the peptide was precipitated by the addition of cold diethyl ether. Crude peptide was collected by one of two methods; filtered, rinsed with cold diethyl ether and eluted off the filter with ammonium hydroxide and lyophilized, or collected by centrifugation. The peptide was dried under high vacuum followed by purification by triturating with acetonitrile and RP-HPLC.

UV-Vis and Photoluminescence.

UV-Vis spectra were recorded using a Varian Cary 50 Bio UV-Vis spectrophotometer. Solution photoluminescence were recorded using a PTi Photon Technology International Fluorometer with a Ushio Xenon short arc lamp. Spectroscopic samples were made by diluting HPLC purified fractions with water to achieve an optical density near 0.08 and the pH was adjusted by the addition aliquots of 1M KOH (for 'basic') or 1M HCl (for 'acidic').

Circular Dichroism (CD).

CD Measurements were recorded at 20° C. using a Jam) J-810 spectropolarimeter. Spectroscopic samples were made by diluting a basic stock solution of known concentration to 0.20 mg/mL and the pH was adjusted by the addition of 10 μL aliquots of 1M KOH or 1M HCl.

Atomic Force Microscopy (AFM).

Samples were analyzed by magnetic tapping mode AFM on an Agilent Technologies PicoSPM LE using probes purchased from Micromasch (NSC18 Co/Cr). Peptide 2 was prepared for AFM as follows: 100 μL of a 0.7 μM aqueous solution was brought to pH 8 with 1M KOH and heated to 75° C. in a sand bath. 14 of 1M HCl was added 2× (30 seconds apart) while agitating. Sample was then removed from heat and allowed to cool for 5 minutes. 10 μL of this sample was added to freshly cleaved mica and allowed to dry before imaging. Peptides 3 and 6 were prepared in the same manner: 200 μL of a 0.08 mM aqueous solution was placed in an acid chamber (closed vial with concentrated HCl) for 20 minutes. 10 μL of this sample was then deposited onto freshly cleaved mica and allowed to dry before imaging.

Attenuated Total Reflectance-Infrared (ATR-IR).

ATR-IR spectra were acquired with an attenuated total reflection device (Pike Technologies MIRacle) equipped with a diamond crystal in single reflection mode using a Mattson Infinity Series FTIR spectrometer with a Mercury cadmium telluride detector (2 $cm^{-1}$ resolution). Each sample was in the solid state used a 4-$cm^{-1}$ resolution and was accumulated for 500 scans, unless otherwise noted.

Electrospray Ionization Mass Spectrometry (ESI-MS).

ESI samples were run in negative mode on a Finnigan LCQ ion trap mass spectrometer with electrospray ionization. Samples were run in a 1:1 MeOH:Water solution with 1% ammonium hydroxide.

Reverse Phase High Performance Liquid Chromatography (RP-HPLC).

RV-HPLC analyses were performed on an Agilent Technologies 1100 Series Quaternary LC System fitted with a Phenomonex C8 column (250×4.6 mm) with a gradient of buffer B/buffer A (see HPLC trace for each peptide for % B/A, buffer A: Ammonium formate buffer pH 8 in water; buffer B: Methanol) over 30-40 minutes with a flow rate of 0.8 mL/min.

Matrix-Assisted Laser Desorption/Ionization Time of Flight (MALDI-TOF). MALDI-TOF spectra were acquired on a Bruker Autoflex III Smartbeam instrument using α-Cyano-4-hydroxycinnamic acid matrix.

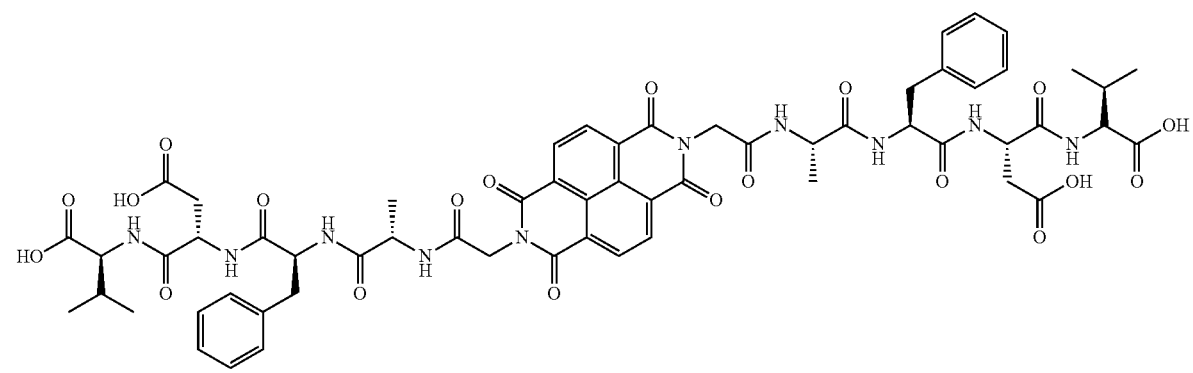

Peptide 1. 1,4,5,8-Naphthalenetetracarboxylic dianhydride (NDA)

(0.008 g, 0.03 mmol) was suspended in pyridine (3 mL) and added to Wang-VDFAG-$NH_2$ resin (0.10 mmol). This mixture was heated to 65° C. followed by the addition of diisopropyl ethyl amine (0.25 mL, 1.5 mmol) and reaction was further heated to 135° C. for 10 hours. A second portion of NDA (0.005 g, 0.02 mmol) was added along with a second portion of pyridine (2 mL). Reaction was maintained at 135° C. and continued for an additional 10 hours. Resin was cooled to room temperature, filtered and washed with MeOH. The resin was then suspended in pyridine (5 mL), heated to 65° C. followed by the addition of diisopropyl ethyl amine (0.25 mL, 1.5 mmol) and further heated to 135° C. for 6 hours. Resin was cooled to room temperature, filtered and washed with one cycle each of H₂O, CH₂Cl₂, 2-propanol, MeOH, NMP, Et₂O and CH₃CN. The resin was cleaved by mixing with 15 mL of a mixture of trifluoroacetic acid (TFA), water and triisopropylsilane (TIPS) (95:2.5:2.5) for 2 hours. Resin was filtered and washed with 5 mL of the cleavage mixture. The filtrate volume was then reduced by 50% under reduced pressure and product was precipitated by the addition of 150 mL Et₂O, and placed in freezer. Pellet was formed by centrifuge. The solid recovered was triturated with Et₂O (2×) and CH₃CN (2×). Filtrate was lyophilized to yield product as brown powder (0.026 g, 0.020 mmol, 41%). ¹H-NMR (400 MHz, d₆-DMSO) δ: 8.71 (4H, s), 7.24 (10H, s), 4.71 (2H, m), 4.56 (2H, m), 4.30 (2H, m), 4.00 (2H, s), 3.06 (2H, m), 2.81 (2H, m), 2.03 (2H, m), 1.15 (6H, d, J=6.80 Hz), 0.82 (12H, s); MS (MALDI-TOF): m/z 1246.136 (M-H⁺), calculated 1246.221. Procedure was modified from literature for a mono-imidation. A. Mokhir, et al., *Bioorganic & Medicinal Chemistry Letters* 13:2489-2492 (2003).

and washed with 5 mL of the cleavage mixture. The filtrate volume was then reduced by 50% under reduced pressure and product was precipitated by the addition of 150 mL Et₂O, and placed in freezer. Pellet was formed by centrifuge. The solid recovered was triturated with Et₂O (2×) and CH₃CN (2×). Filtrate was lyophilized to yield product as black powder (0.020 g, 0.015 mmol, 29%). ¹H-NMR (300 MHz, d₆-DMSO, 90° C.) δ: 8.96 (4H, d, J=7.9 Hz), 8.63 (4H, d, J=7.8 Hz), 7.27 (10H, s), 4.80 (4H, s), 4.58 (8H, m), 4.34 (4H, m), 4.15 (4H, broad), 2.07 (6H, m), 1.24 (6H, d, J=6.8 Hz), 1.01 (2H, m), 0.89 (12H, d, J=6.7 Hz); MS (ESI−) m/z 684.01 (M-2H⁺) (calc. 684.24), m/z 455.81 (M-3H⁺) (calc. 455.83). Procedure was modified from literature for a mono-imidation. A. Mokhir, et al., *Bioorganic & Medicinal Chemistry Letters* 13:2489-2492 (2003).

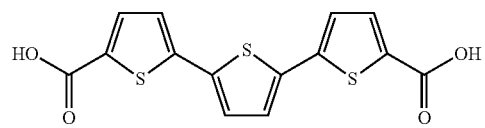

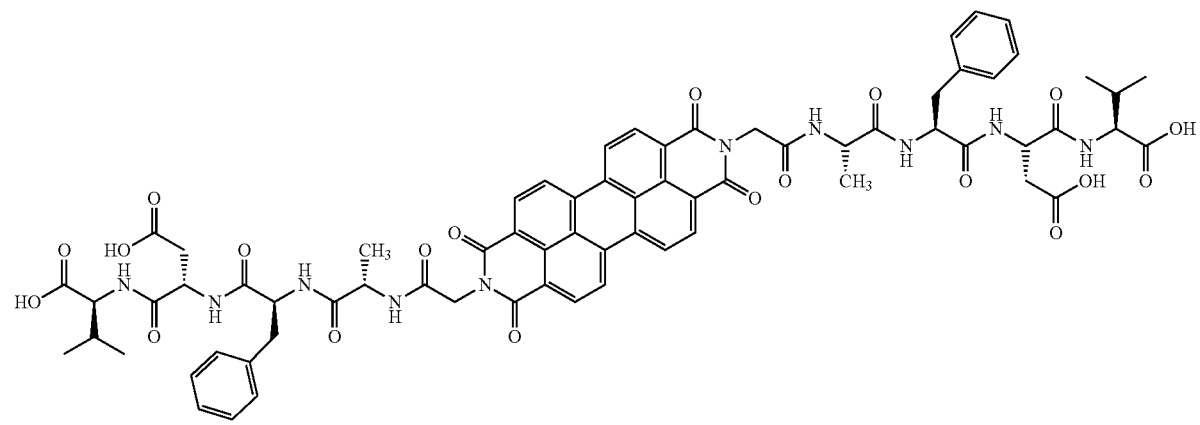

Peptide 2. 3,4,9,10-Perylenetetracarboxylic dianhydride (PDA)

[2,2':5',2''-terthiophene]-5,5''-dicarboxylic acid (OT-3 diacid)

(0.012 g, 0.031 mmol) was suspended in pyridine (3 mL) and added to Wang-VDFAG-NH₂ resin (0.10 mmol). This mixture was heated to 65° C. followed by the addition of diisopropyl ethyl amine (0.25 mL, 1.5 mmol) and reaction was further heated to 135° C. for 10 hours. A second portion of PDA (0.008 g, 0.02 mmol) was added along with a second portion of pyridine (2 mL). Reaction was maintained at 135° C. and continued for an additional 10 hours. Resin was cooled to room temperature, filtered and washed with MeOH. The resin was then suspended in pyridine (5 mL), heated to 65° C. followed by the addition of diisopropyl ethyl amine (0.25 mL, 1.5 mmol) and further heated to 135° C. for 6 hours. Resin was cooled to room temperature, filtered and washed with one cycle each of H₂O, CH₂Cl₂, 2-propanol, MeOH, NMP, Et₂O and CH₃CN. The resin was cleaved by mixing with 15 mL of a mixture of trifluoroacetic acid (TFA), water and triisopropylsilane (TIPS) (95:2.5:2.5) for 2 hours. Resin was filtered (0.739 g, 2.98 mmol) of 2,2':5',2''-terthiophene was added to a flame dried two-neck round bottom flask and the flask was evacuated and refilled with N₂ (3×). 36 mL of dry THF was then added and reaction degassed with N₂ for 10 minutes. The reaction mixture was cooled to −78° C. and 11.4 mL of ⁿBuLi in hexane (1.63 M, 18.6 mmol) was added dropwise. The reaction mixture was allowed to warm to 0° C. and stirred for two hours. The reaction was then cooled down to −78° C. and solid carbon dioxide was added and stirring was continued for two hours at −78° C. and then 18 hours at room temperature. The solid produced was filtered, washed with excess 3% HCl and acetone then dried in vacuum. The product was obtained as a yellow solid (0.934 g, 2.77 mmol, 93%). Procedure adapted from and characterization data matches literature. Z. Ni, et al., *J. Am. Chem. Soc.* 127:12752-12753 (2005).

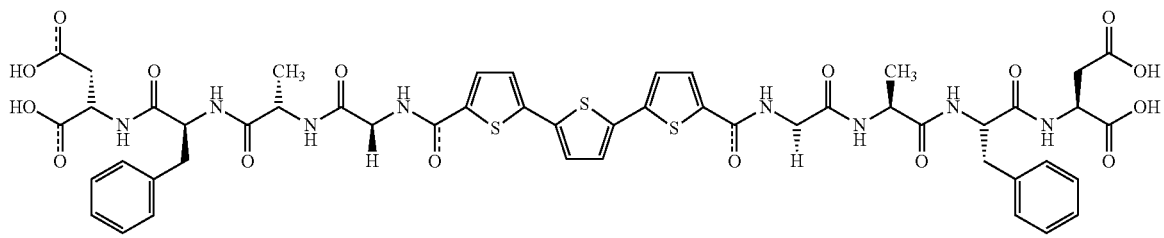

Peptide 3

0.010 g (0.028 mmol) of OT-3 diacid and (0.031 g, 0.060 mmol) of PyBOP was dissolved in 10 mL 2:1 NMP:$CH_2Cl_2$, then 0.174 mL of DIPEA (0.998 mmol) was added and agitated by vortex for 30 seconds. The solution was then added to Wang-DFAG-$NH_2$ resin (0.1 mmol reactive —$NH_2$) in a peptide chamber and the reaction was mixed for 18 hours. The resin was rinsed thoroughly with NMP and $CH_2Cl_2$, then mixed for 10 minutes in NMP, and rinsed again with NMP and $CH_2Cl_2$. The resin was subjected to a second round of coupling: 0.007 g (0.02 mmol) of OT-3 diacid and 0.021 g (0.040 mmol) of PyBOP was dissolved in 10 mL 2:1 NMP:$CH_2Cl_2$, then 0.174 mL of DIPEA (0.998 mmol) was added and stirred for 30 seconds. The solution was then added to the resin in a peptide chamber and the reaction was mixed for 18 hours. The resin was rinsed thoroughly with NMP and $CH_2Cl_2$, then mixed for 10 minutes in NMP, and rinsed again with NMP and $CH_2Cl_2$. The resin was then washed with $CH_2Cl_2$, NMP, acetic acid, and MeOH and placed under high vacuum to dry. The resin was cleaved by mixing with 10 mL of a mixture of trifluoroacetic acid (TFA), water and triisopropylsilane (TIPS) (95:2.5:2.5) for two hours. Resin was filtered and washed with 5 mL of the cleavage mixture. The filtrate volume was then reduced by 50% under reduced pressure and product was precipitated by the addition of 150 mL $Et_2O$, and placed in freezer. Pellet was formed by centrifuge. The solid recovered was triturated with $Et_2O$ (2×) and $CH_3CN$ (2×). Crude peptide was obtained as a yellow powder (0.021 g, 0.019 mmol, 38%). $^1$H NMR (400 MHz, $D_2O$) δ: 7.34-6.99 (m, 14H), 6.51 (broad, 4H), 4.62 (2H, m), 4.44 (s, 2H) 4.30 (2H, d, J=7.0 Hz), 3.92 (4H, m), 3.23 (2H, d, J=10.0 Hz), 2.93 (2H, t, J=9.0 Hz), 2.70 (broad, 4H), 1.27 (6H, d, J=6.6 Hz). MS (ESI−) m/z 1115.3 (M-H$^+$) (calc. 1115.3), m/z 1137.2 (M-2H$^+$+Na$^+$) (calc. 1137.2), m/z 1159.2 (M-3H$^+$+2Na$^+$) (calc. 1159.2), m/z 556.9 (M-2H$^+$) (calc. 557.1), m/z 567.9 (M-2H$^+$) (calc. 568.1).

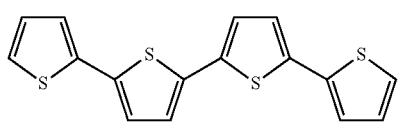 [SMILES: c1csc(-c2ccc(-c3ccc(-c4cccs4)s3)s2)c1]

2,2':5',2":5",2'''-quaterthiophene (OT-4)

5,5'-bis(tributylstannyl)-2,2'-bithiophene (2.16 g, 2.90 mmol) was dissolved in dry DMF (45 mL) and transferred via cannula to Pd(PPh$_3$)$_4$ (0.101 g, 0.087 mmol) in a Schlenk flask. 2-bromothiophene (1.14 g, 6.96 mmol) was added via syringe and the solution was degassed with nitrogen. Reaction was then heated to 90° C. for 18 hours. Reaction was quenched with water, extracted with chloroform (3×), and the combined organics washed with brine. Organics were dried with magnesium sulfate and concentrated by rotary evaporator yielding crude material as a waxy orange solid. The solid was recrystallized from boiling toluene and collected by filtration. Filtered solid was then redissolved in boiling chloroform and stirred with activated charcoal for 15 minutes. The charcoal was removed by filtering through celite and the chloroform removed by rotary evaporator to yield product as a yellow solid (0.676 g, 2.05 mmol, 70%). Characterization data matches literature. Z. H. Li, et al., *Org. Lett.* 9:3659-3662 (2007).

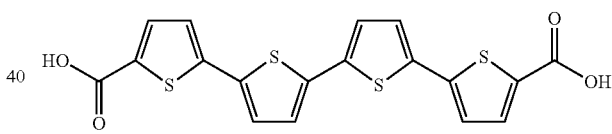

[2,2':5',2":5",2'''-quaterthiophene]-5,5'''-dicarboxylic acid (OT-4 diacid)

0.200 g (0.605 mmol) of 2,2':5',2":5",2'''-quaterthiophene (OT-4) was added to a flame dried two-neck round bottom flask and the flask was evacuated and refilled with $N_2$ (3×). 20 mL of dry THF was then added and reaction degassed with $N_2$ for 10 minutes. The reaction mixture was cooled to −78° C. and 2.36 mL of "BuLi in hexane (1.60 M, 3.78 mmol) was added dropwise. The reaction mixture was allowed to warm to 0° C. and stirred for 2 hours. The reaction was then cooled down to −78° C. and solid carbon dioxide was added and stirring was continued for 2 hours at −78° C. and then 18 hours at room temperature. The solid produced was filtered, washed with excess 3% HCl and acetone then dried in vacuum. Procedure adapted from literature. Z. Ni, et al., *J. Am. Chem. Soc.* 127:12752-12753 (2005). The product was obtained as a yellow/orange solid (0.182 g, 0.435 mmol, 72%) and used without further purification.

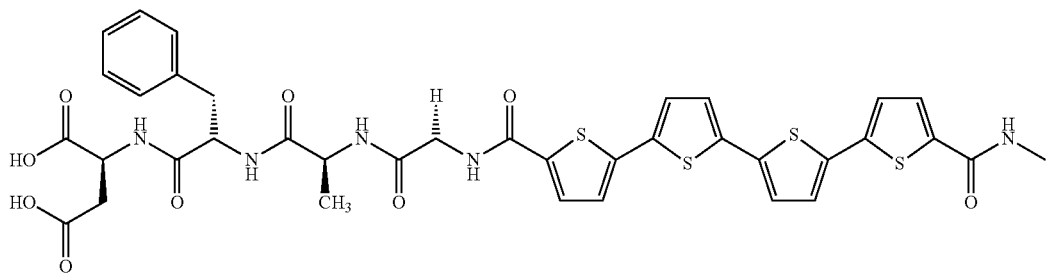

Peptide 4

0.013 g (0.031 mmol) of OT-4 diacid and 0.031 g (0.060 mmol) of PyBOP was dissolved in 10 mL NMP, then 0.174 mL of DIPEA (0.998 mmol) was added and mixed by vortex for 30 seconds. The solution was then added to Wang-DFAG-NH$_2$ resin (0.1 mmol reactive —NH$_2$) in a peptide chamber and the reaction was mixed for 18 hours. The resin was rinsed thoroughly with NMP and CH$_2$Cl$_2$, then stirred for 10 minutes in NMP, and rinsed again with NMP and CH$_2$Cl$_2$. The resin was subjected to a second round of coupling: 0.008 g (0.02 mmol) of OT-4 diacid and 0.021 g (0.040 mmol) of PyBOP was dissolved in 10 mL NMP, then 0.174 mL of DIPEA (0.998 mmol) was added and stirred for 30 seconds. The solution was then added to the resin in a peptide chamber and the reaction was mixed for 18 hours. Final cleavage from the resin was performed as described for peptide 3. Crude peptide was obtained as a yellow powder (0.027 g, 0.023 mmol, 45%). $^1$H NMR (400 MHz, D$_2$O) δ: 7.34-7.26 (18H, m), 4.39-4.36 (5H, m), 4.22-4.20 (1H, m), 4.09 (3H, q, J=7.7 Hz), 3.95 (9H, q, J=13.4 Hz), 3.53 (2H, s), 3.40-3.27 (5H, m), 2.92 (5H, q, J=13.7 Hz), 2.68-2.53 (13H, m), 2.05 (2H, s), 1.33-1.18 (6H, broad), 1.07 (6H, d, J=7.7 Hz) MS (ESI−) m/z 1197.4 (M-H$^+$) (calc. 1197.2), m/z 1219.1 (M-2H$^+$+Na$^+$) (calc. 1219.2), m/z 597.9 (M-2H$^+$) (calc. 598.1). MS (ESI−) m/z 1197.4 (M-H$^+$) (calc. 1197.2), m/z 1219.1 (M-2H$^+$+Na$^+$) (calc. 1219.2), m/z 597.9 (M-2H$^+$) (calc. 598.1).

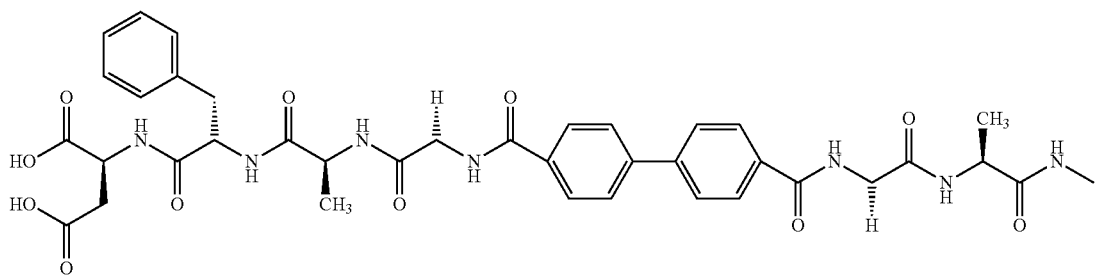

Peptide 5

0.007 g (0.03 mmol) of [1,1'-biphenyl]-4,4'-dicarboxylic acid and 0.031 g (0.060 mmol) of PyBOP was dissolved in 10 mL 2:1 NMP:CH$_2$Cl$_2$, then 0.174 mL of DIPEA (0.998 mmol) was added and stirred for 30 seconds. The solution was then added to Wang-DFAG-NH$_2$ resin (0.1 mmol reactive —NH$_2$) in a peptide chamber and the reaction was mixed for 18 hours. The resin was rinsed thoroughly with NMP and CH$_2$Cl$_2$, then stirred for 10 minutes in NMP, and rinsed again with NMP and CH$_2$Cl$_2$. The resin was subjected to a second round of coupling: 0.005 g (0.02 mmol) of [1,1'-biphenyl]-4,4'-dicarboxylic acid and 0.021 g (0.040 mmol) of PyBOP was dissolved in 10 mL 2:1 NMP:$CH_2Cl_2$, then 0.174 mL of DIPEA (0.998 mmol) was added and stirred for 30 seconds. The solution was then added to the resin in a peptide chamber and the reaction was mixed for 18 hours. Final cleavage from the resin was performed as described for peptide 3. Crude peptide was obtained as an off-white powder (0.023 g, 0.023 mmol, 45%). $^1$H NMR (400 MHz, $D_2O$) δ: 7.81 (4H, d, J=8.44 Hz), 7.67 (4H, d, J=8.56 Hz), 7.23 (10H, m), 4.67 (2H, m), 4.38 (2H, m), 4.27 (2H, m), 4.03 (4H, m), 3.25 (2H, dd, J=14.17, 4.76 Hz), 2.92 (2H, m), 2.61 (4H, m), 1.21 (6H, d, J=7.16 Hz); MS (ESI−) m/z 1043.3 (M-2H$^+$+Na$^+$) (calc. 1043.3), m/z 1065.4 (M-3H$^+$+2Na$^+$) (calc. 1065.3), m/z 509.9 (M-2H$^+$) (calc. 510.2), m/z 520.8 (M-3H$^+$+Na$^+$) (calc. 521.2), m/z 531.9 (M-4H$^+$+2Na$^+$) (calc. 532.2).

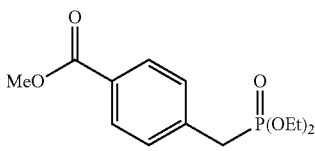

Methyl 4-((diethoxyphosphoryl)methyl)benzoate

To a solution of methyl 4-methylbenzoate (2.01 g, 13.3 mmol) and 1,2-dichloroethane (100 mL) was added benzoyl peroxide (catalytic amount) and NBS (2.84 g, 16.0 mmol). The resulting mixture was heated to reflux while being stirred under nitrogen. After three hours, another catalytic amount of benzoyl peroxide was added and the mixture was refluxed for an additional three hours. The reaction mixture was allowed to cool to RT, followed by the addition of $Et_2O$ (20 mL) and filtration of a solid which precipitated out of solution. The filtrate was washed with water (2×) and brine (2×), dried over $MgSO_4$, filtered and the solvent was removed under reduced pressure to give a light yellow clear oil. Triethyl phosphite (2.28 mL, 13.3 mmol) was added to the oil and the reaction was stirred under nitrogen at 160° C. for three hours. Excess triethyl phosphite was distilled off and the product was purified by column chromatography (EtOAc) to give a transparent light yellow oil (2.28 g, 7.97 mmol, 60%). Characterization data matches literature. E. N. Durantini, *Synthetic Communications*, 29:4201-4222 (1999).

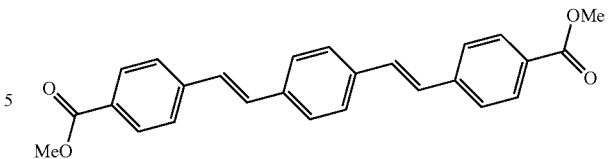

Dimethyl 4,4'-((1E,1'E)-1,4-phenylenebis(ethene-2,1-diyl))dibenzoate (OPV-3 diester)

A solution of Methyl 4-((diethoxyphosphoryl)methyl)benzoate (2.02 g, 7.05 mmol) and terepthaldehyde (0.462 g, 3.44 mmol) in THF (12 mL) was added to a suspension of NaOMe (1.12 g, 20.6 mmol) in THF (70 mL). The reaction was stirred under nitrogen for four hours and was then neutralized with 1M HCl. The resulting suspension was filtered, the collected solid was washed with THF, EtOH, and $H_2O$, then allowed to dry under vacuum to give a yellow solid (1.15 g, 2.88 mmol, 84%). Characterization data matches literature. J. C. Sancho-García, et al., *J. Phys. Chem. B*, 109:4872-4880 (2005).

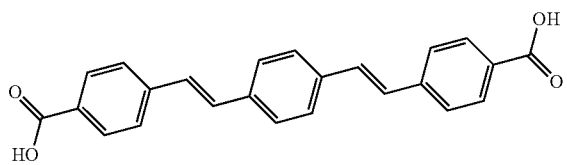 [SMILES: O=C(O)c1ccc(/C=C/c2ccc(/C=C/c3ccc(C(=O)O)cc3)cc2)cc1]

4,4'-(1E,1'E)-1,4-phenylenebis(ethene-2,1-diyl))dibenzoic acid (OPV-3 diacid)

A suspension of OPV-3 diester (0.501 g, 1.25 mmol) in 3:1 EtOH/$H_2O$ (16 mL), KOH (0.352 g, 6.27 mmol) was added and the suspension was refluxed under nitrogen for 2 days. The reaction mixture was allowed to cool and the solvent was removed under reduced pressure and the resulting carboxylate salt was taken up in hot $H_2O$ (80 mL) and acidified with conc. HCl. The resulting solid was filtered, washed with water then allowed to dry to give a yellow solid (0.425 g, 1.15 mmol, 92%). Due to the extremely low solubility of this compound it was not possible to obtain NMR data. HRMS (EI/CI) m/z calculated for ($C_{24}H_{18}O_4$) 370.1205. found 370.1206. UV-Vis ($H_2O$): $\lambda_{max}$=366 nm.

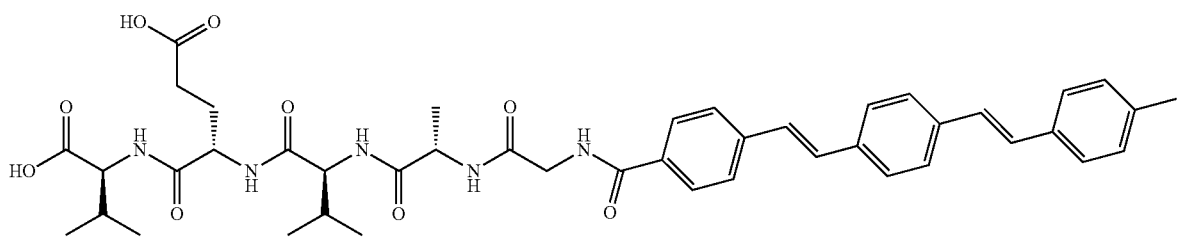

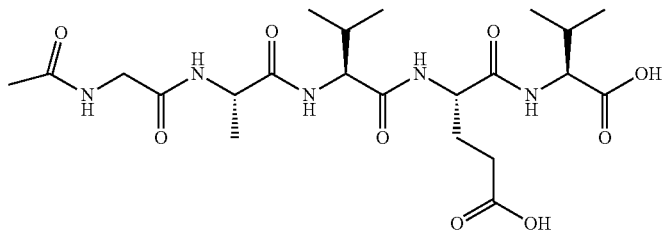

Peptide 6

A solution of OPV-3 diacid (0.025 g, 0.069 mmol) and PyBOP (0.071 g, 0.14 mmol) was dissolved in a 2:1 solution of NMP/CH$_2$Cl$_2$ (10 mL), once dissolved DIPEA (278 µL, 1.60 mmol) was added and the solution was stirred for one minute. This solution was added to Wang-VEVAG-NH$_2$ resin (0.228 mmol) that had been previously allowed to swell in CH$_2$Cl$_2$ for 10 minutes. The resulting mixture was gently agitated for 12 hours. The reaction mixture was then filtered and the resin was washed with NMP, CH$_2$Cl$_2$, and MeOH a total of three times. A second coupling solution of OPV-3 diacid (0.017 g, 0.046 mmol) and PyBOP (0.048 g, 0.091 mmol) in 2:1 NMP/CH$_2$Cl$_2$ (10 mL) followed by DIPEA (278 µL, 1.60 mmol) was added to the resin and gently agitated for 12 hours. The resin was washed as previously described and a blank coupling cycle with PyBOP (0.071 g, 0.137 mmol) with DIPEA (278 µL, 1.60 mmol) in 2:1 NMP/CH$_2$Cl$_2$ (10 mL) was allowed to react for one hour and the resin was washed as previously described. The resin was cleaved in a 1:1 solution of CH$_2$Cl$_2$/cleavage cocktail (95:2.5:2.5 TFA/TIPS/H$_2$O) (10 mL) for two hours. This solution was filtered out and the resin was washed with CH$_2$Cl$_2$ (10 mL), the filtrate was evaporated until 50% of the total volume remained, then 90 mL of cold Et$_2$O was added. The precipitated peptide was centrifuged and the remaining solution was decanted off. This was repeated with 45 mL of cold Et$_2$O, and then twice with 45 mL of cold MeCN. The final centrifuged peptide was then lyophilized to give a yellow solid (0.070 g, 0.05 mmol, 48%). $^1$H NMR (400 MHz, d$_6$-DMSO) δ: 7.90 (4H, d, J=8.0 Hz), 7.70 (4H, d, J=8.8), 7.67 (4H, s), 7.51 (2H, d, J=16.4 Hz), 7.35 (4H, d, J=16.8 Hz), 4.39 (2H, m), 4.26 (2H, m), 4.15 (2H, m), 3.87 (4H, m), 2.20 (4H, m), 2.01 (4H, m), 1.86 (2H, m), 1.76 (2H, m), 1.22 (6H, d, J=6.8 Hz), 0.82 (24H, m). MS (ESI−) m/z 1280.6 (M-H$^+$) (calc. 1279.6), m/z 675.8 (M-4H$^+$+2K$^+$) (calc. 677.24), m/z 656.8 (M-3H$^+$+K$^+$) (calc. 658.3), m/z 639.4 (M-2H$^+$) (calc. 639.3).

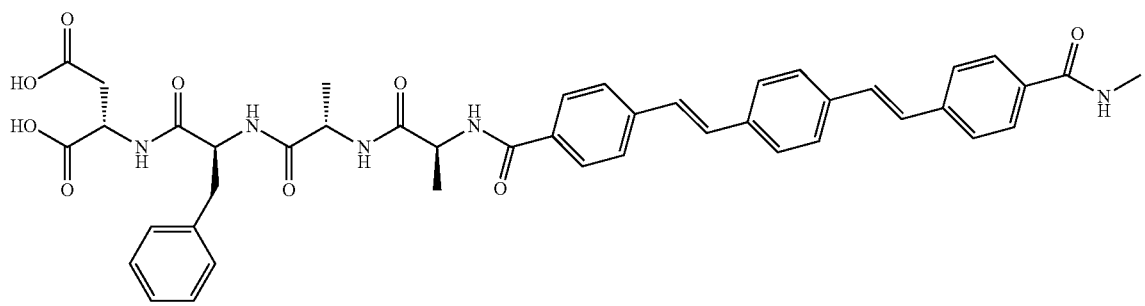

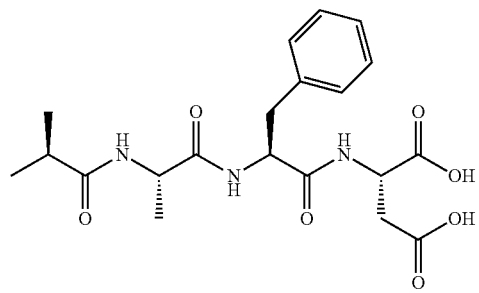

Peptide 7

A solution of OPV-3 diacid (0.010 g, 0.026 mmol) and PyBOP (0.027 g, 0.052 mmol) was dissolved in a 2:1 solution of NMP/CH$_2$Cl$_2$ (10 mL), once dissolved DIPEA (104 µL, 0.597 mmol) was added and the solution was stirred for one minute. This solution was added to Wang-DFAA-NH$_2$ resin (0.0896 mmol) that had been previously allowed to swell in CH$_2$Cl$_2$ for 10 minutes. The resulting mixture was gently agitated for 12 hours. The reaction mixture was then filtered and the resin was washed with NMP, CH$_2$Cl$_2$, and MeOH three times each. A second coupling solution of OPV-3 diacid (0.006 g, 0.02 mmol) and PyBOP (0.018 g, 0.034 mmol) in 2:1 NMP/CH$_2$Cl$_2$ (10 mL) followed by DIPEA (104 µL, 0.597 mmol) was added to the resin and gently agitated for 12 hours. The resin was washed as previously described and was cleaved in a 1:1 solution of CH$_2$Cl$_2$/cleavage cocktail (95:2.5:2.5 TFA/TIPS/H$_2$O) (10 mL) for two hours. This solution was filtered out and the resin was washed with CH$_2$Cl$_2$ (10 mL), the filtrate was evaporated until 50% of the total volume remained, then 90 mL of cold Et$_2$O was added. The precipitated peptide was centrifuged and the remaining solution was decanted off. This step was repeated with 45 mL of cold Et$_2$O, and then twice with 45 mL of cold MeCN. The final centrifuged peptide was then lyophilized to give a yellow solid (0.030 g, 0.020 mmol, 30%). $^1$H NMR (400 MHz, D$_2$O) δ: 7.80 (4H, d, J=8.0 Hz), 7.70 (4H, d, J=8.0 Hz), 7.67 (4H, s), 7.51 (2H, d, J=16.4 Hz), 7.35 (4H, d, J=16.8 Hz), 4.39 (2H, m), 4.26 (2H, m), 4.15 (2H, m), 3.87 (4H, m), 2.20 (4H, m), 2.01 (4H, m), 1.86 (2H, m), 1.76 (2H, m). 1.22 (6H, d, J=6.8 Hz), 0.82 (24H, m). MS (ESI−) m/z 1177.7 (M-H$^+$) (calc. 1177.5), m/z 588.3 (M-2H) (calc. 588.2).

agitated for 12 hours. The reaction mixture was then filtered and the resin was washed with NMP, CH$_2$Cl$_2$, and MeOH a total of three times. A second coupling solution of OPV-3 diacid (0.007 g, 0.018 mmol) and PyBOP (0.019 g, 0.037 mmol) in 2:1 NMP/CH$_2$Cl$_2$ (10 mL) followed by DIPEA (112 µL, 0.643 mmol) was added to the resin and gently agitated for 12 hours. The resin was washed as previously described and was cleaved in a 1:1 solution of CH$_2$Cl$_2$/cleavage cocktail (95:2.5:2.5 TFA/TIPS/H$_2$O) (10 mL) for two hours. This solution was filtered out and the resin was washed with CH$_2$Cl$_2$ (10 mL), the filtrate was evaporated until 50% of the total volume remained, then 90 mL of cold Et$_2$O was added. The precipitated peptide was centrifuged and the remaining solution was decanted off. This was repeated with 45 mL of cold Et$_2$O, and then twice with 45 mL of cold MeCN. The final centrifuged peptide was then lyophilized to give a yellow solid (0.043 g, 0.03 mmol, 35%). $^1$H NMR (400 MHz, d$_6$-DMSO) δ: 7.78 (4H, d, J=8.4 Hz), 7.66 (8H, m), 7.36 (4H, m), 7.23 (12H, m), 7.15 (8H, m), 4.70 (2H, m), 4.48 (2H, m), 4.29 (4H, m), 3.06 (5H, m), 2.95 (2H, m), 2.8 (4H, m), 1.25 (6H, d, J=7.2 Hz). MS (ESI−) m/z 1329.5 (M-H$^+$) (calc. 1329.5), m/z 664.2 (M-2H$^+$) (calc. 664.3).

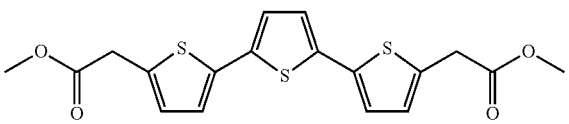

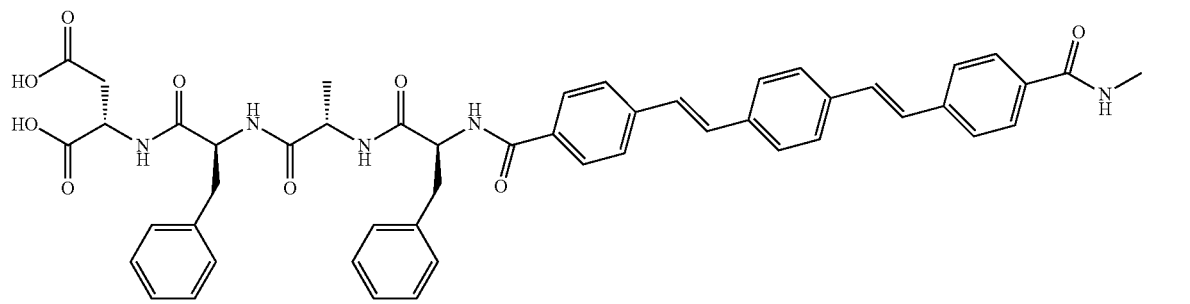

Peptide 8

A solution of OPV-3 diacid (0.010 g, 0.028 mmol) and PyBOP (0.029 g, 0.055 mmol) was dissolved in a 2:1 solution of NMP/CH$_2$Cl$_2$ (10 mL), once dissolved DIPEA (112 µL, 0.643 mmol) was added and the solution was stirred for one minute. This solution was added to Wang-DFAF-NH$_2$ resin (0.0992 mmol) that had been previously allowed to swell in CH$_2$Cl$_2$ for 10 minutes. The resulting mixture was gently

Dimethyl 2,2'-([2,2':5',2"-terthiophene]-5,5"-diyl) diacetate (OT-3-CH$_2$-diester)

A flame dried Schlenk flask was cooled under vacuum, refilled with nitrogen and charged with Pd(PPh$_3$)$_4$ (0.279 g, 0.241 mmol). The flask was then evacuated and refilled with N$_2$. Degassed dioxane (20.0 mL) was cannulated in to a flame-dried round bottom flask followed by the addition of bisstannylated thiophene, J. Hou, et al., *J. Am. Chem. Soc.*

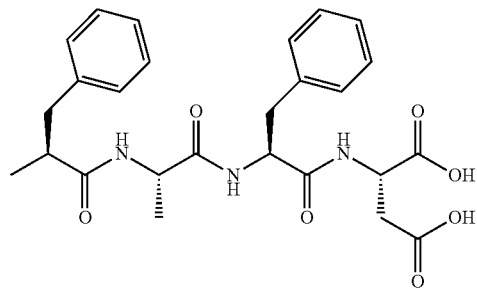

128:4911-4916 (2006), (4.00 g, 6.04 mmol) and brominated thiophene methyl ester, S. R. Diegelmann, et al., *J. Am. Chem. Soc.* 130:13840-13841 (2008), (4.26 g, 18.1 mmol). The reaction was degassed for 20 minutes then heated to 80° C. and stirred for 48 hours. The reaction was cooled to room temperature, diluted with EtOAc, stirred with 1M KF for 10 minutes and filtered through celite. The organic phase was then washed with brine (3×) and water (2×), dried with magnesium sulfate, stirred with charcoal for 20 minutes, filtered through celite again, and concentrated under reduced pressure. The crude material was triturated with hexanes, concentrated, and purified by a silica column chromatography (gradient 20% to 25% EtOAc:hexanes). Final product was obtained as a brown solid (0.837 g, 2.13 mmol, 35%). $^1$H NMR (400 MHz, CDCl$_3$) δ: 7.00 (4H, t, J=3.4 Hz), 6.84 (2H, d, J=3.4 Hz), 3.81 (4H, s), 3.75 (6H, s). $^{13}$C NMR (100 MHz, CDCl$_3$) δ: 170.5, 136.8, 135.9, 134.2, 127.6, 124.0, 123.2, 52.3, 35.4.

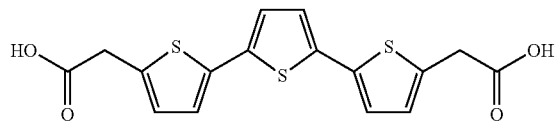 [SMILES: O=C(O)Cc1ccc(-c2ccc(-c3ccc(CC(=O)O)s3)s2)s1]

2,2'-([2,2':5',2''-terthiophene]-5,5''-diyl)diacetic acid (OT-3-CH$_2$-diacid)

OT-3-CH$_2$-diester (0.837 g, 2.13 mmol) was dissolved in 50 mL diethyl ether and to that was added 15 mL MeOH and 25 mL of 1M KOH (aq). The solution was then stirred for 18 hours at room temperature. The reaction was then acidified with 1M HCl to pH 3 and the organics removed under reduced pressure. The crude material was filtered, washed with excess water, eluted off the filter with 1:1 MeOH:acetone, dried with magnesium sulfate, concentrated under reduced pressure, and triturated with hot hexanes. The product was isolated as a brown solid (0.685 g, 1.88 mmol, 88%). $^1$H NMR (400 MHz, CDCl$_3$) δ: 12.70 (2H, broad), 7.19-6.91 (6H, m), 3.84 (4H, s). $^{13}$C NMR (100 MHz, CDCl$_3$) δ: 171.4, 136.0, 135.2, 135.2, 127.9, 124.4, 123.5, 35.1. HRMS (FAB) m/z calculated for (C$_{16}$H$_{12}$O$_4$S$_3$)$^+$363.9898. found 393.9899.

Example 3

Formation of Assembled Nanostructures In Vivo and In Vitro Uses of Assembled Nanostructures A physiologically buffered solution of the presently disclosed peptide-[organic electronic unit (e.g., a quaterthiophene)]-peptide molecules could be introduced in vivo by way of injection, where upon contact with ions in a bodily fluid, for example, spinal fluid, and the like, would trigger assembly of a dense hydrogel mass composed of the presently disclosed nanostructures. Application of an external electric field would act as a "gate electrode" in the context of organic semiconductors, and allow for the injection of mobile charge carriers within the nanostructure. It is expected that the extent of field-induced mobile charges would be sufficient to change the wettability (and thus attenuate cell adhesion or the extension of neuronal processes), or alter the responsiveness of the artificial construct to detect alterations in electrical potential among cells. Thus, in the event that a true synapse is unable to be re-established following a traumatic injury, the expectation is that the presently disclosed nanostructures, once field-effect doped into a conductive form, would respond to the firing of an ion channel of one nerve cell (or other communicating cell type) and transmit this stimulus by virtue of the underlying ionically conductive channel to another cell located further away along the nanostructure.

In some embodiments, the π-conjugated unit comprises a chromophore and peptide-chromophore-peptide units could be processed as described immediately hereinabove and photophysically doped into a conductive state using low energy visible excitation. This step would minimize the need for electrical fields directly. Further, it also is contemplated that a chemical redox process could be used as a mechanism for imparting electrical conductivity, provided that the chemical redox agent would not interfere with or be acted upon by biological redox agents.

Representative molecular structures including different types of organic electronic units are presented below:

Oligothiophenes:

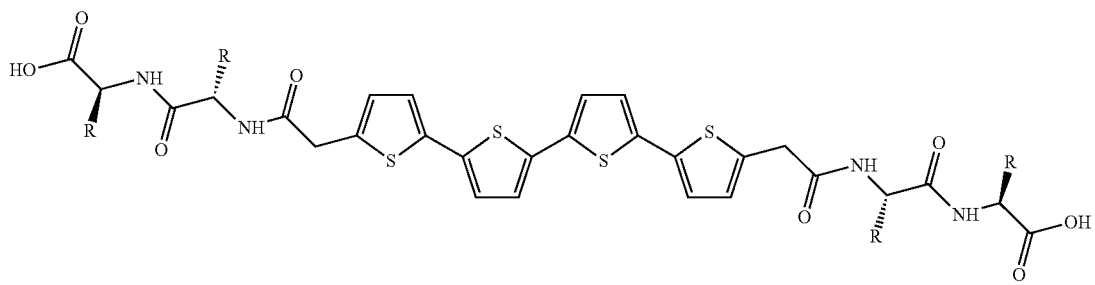

Oligo(phenylene vinylene) chromophores:

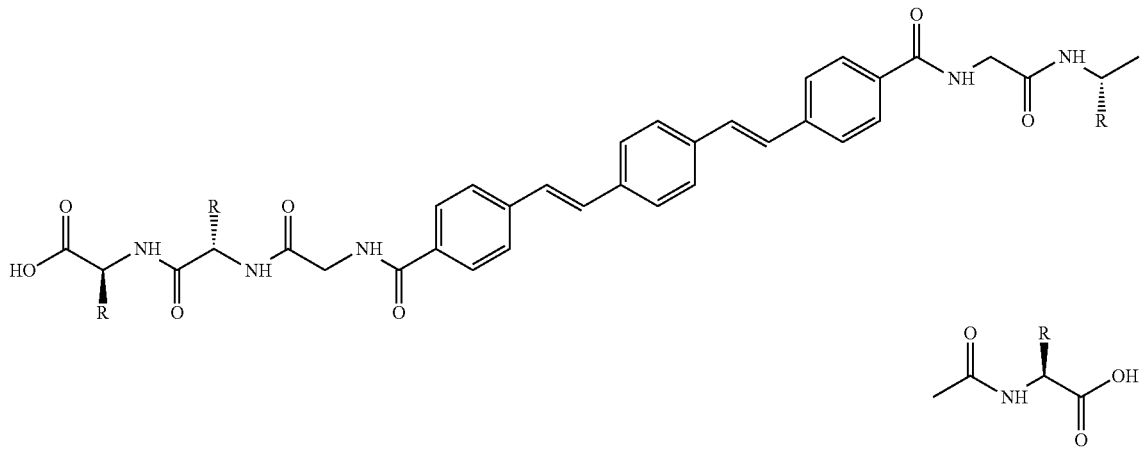

Perylene diimide chromophore (and unit for electron transport)

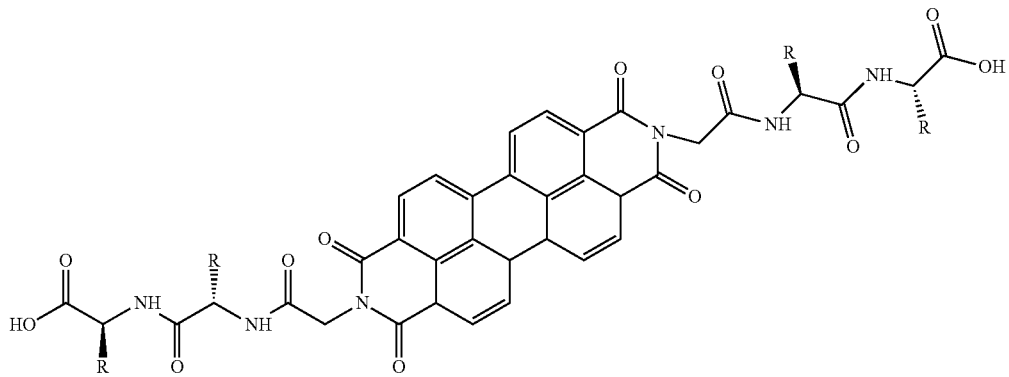

The peptide-chromophore-peptide would be designed with a specific peptide sequence known or hypothesized to play a role in cell differentiation, and the effects of this regulation would be subject to external control (photophysical excitation or field-effect doping) such that the extent of differentiation, or the direction of the differentiation, could be controlled. This process could be employed in vitro through the preparation of hydrogel scaffolds that encapsulate cells, and the bulk gels then could be exposed to electrical fields or visible light energy.

Peptide-chromophore-peptide molecules where the chromophore has an environmentally sensitive photophysical or electrical response would be used as probes to study the uptake of the amyloid-forming material in the presence of natural amyloid forming peptides. Thus, once the amyloid formed, a defined physical observable (shift in the wavelength of emitted or absorbed light, changes in redox properties) would be correlated to the association within the amyloid nanostructure.

Further, individual nanostructures would be patterned or aligned using common techniques, such as AC dielectrophoresis. Cells would then be cultured with defined spatial placement and the intercellular communication would be probed as mediated by electronic and/or ionic transmission of impulses through the underlying nanostructure framework. This process would be amenable to field-induced and photophysical generation of mobile charge carriers and would be an in vitro tool to understand how this might be achieved in vivo.

Further, the presentation of the peptide signal can be varied by the synthetic procedure used to construct the molecules. For example, in some embodiments, the use of non-symmetric π-conjugated units will lead to the formation of different exposed terminal groups (one carboxylic acid and one amine) or, in other embodiments, carboxylic acids are presented at both ends through the use of a symmetric π-conjugated unit that undergoes on-resin dimerization. This dual approach allows for control over how the bioactive signal is presented to biological environments and allows for biomolecular recognition to be optimized. For example, the periphery could be decorated with HOOC-Asp-Gly-Arg (DGR) or HOOC-Arg-Gly-Asp (RGD) through the presently disclosed on-resin dimerization, or with mixed signals that present both COOH— and NH$_2$-terminated signals if the initial strategy disclosed herein is used.

For example, the presently disclosed on-resin dimerization approach can be used to present a HOOC-(DGR) tripeptide:

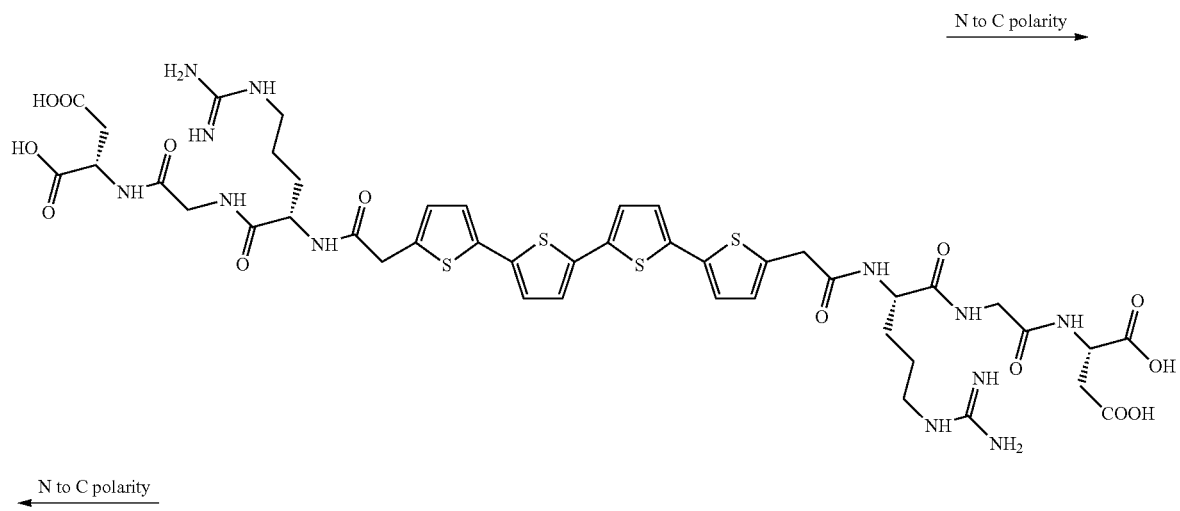 [SMILES: N=C(N)NCCC[C@H](NC(=O)Cc1ccc(-c2ccc(-c3ccc(-c4ccc(CC(=O)N[C@@H](CCCNC(=N)N)C(=O)NCC(=O)N[C@@H](CC(=O)O)C(=O)O)s4)s3)s2)s1)C(=O)NCC(=O)N[C@@H](CC(=O)O)C(=O)O]

And both amine and carboxylic acid presentation using the original synthesis procedure disclosed herein:

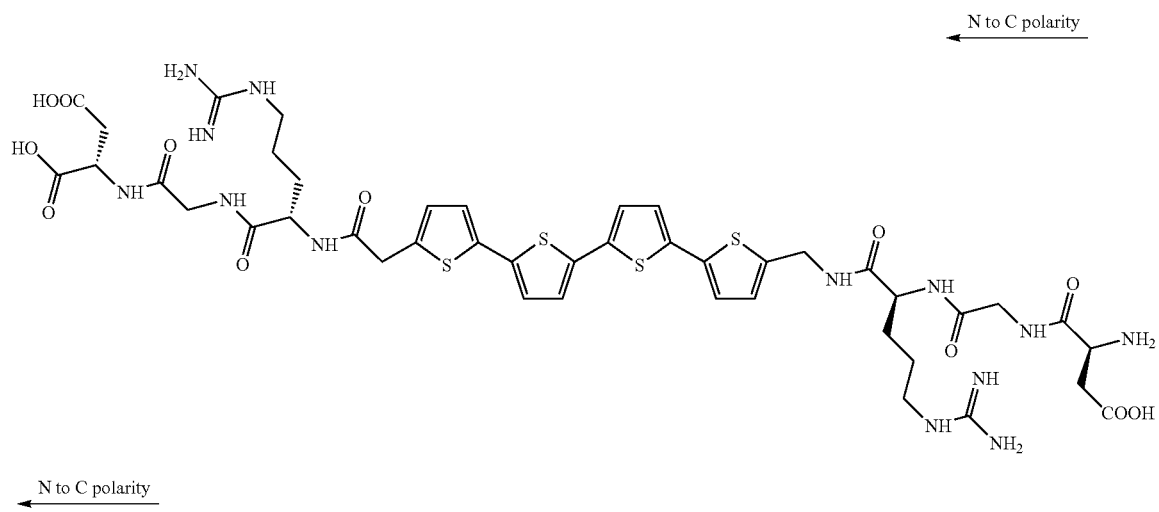 [SMILES: N=C(N)NCCC[C@H](NC(=O)CNC(=O)[C@@H](N)CC(=O)O)C(=O)NCc1ccc(-c2ccc(-c3ccc(-c4ccc(CC(=O)N[C@@H](CCCNC(=N)N)C(=O)NCC(=O)N[C@@H](CC(=O)O)C(=O)O)s4)s3)s2)s1]

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Schoonbeek, F. S., van Esch, J. H., Wegewijs, B., Rep, D. B. A., de Haas, M. P., Klapwijk, T. M., Kellogg, R. M., and Feringa, B. L. Angew. Chem., Int. Ed. 1999 38 1393-1397.

Hill, J. P., Jin, W. S., Kosaka, A., Fukushima, T., Ichihara, H., Shimomura, T., Ito, K., Hashizume, T., Ishii, N., and Aida, T. Science 2004 304 1481-1483.

Leclere, P., Surin, M., Viville, P., Lazzaroni, R., Kilbinger, A. F. M., Henze, O., Feast, W. J., Cavallini, M., Biscarini, F., Schenning, A. P. H. J., and Meijer, E. W. Chem. Mater. 2004 16 4452-4466.

Hoeben, F. J. M., Jonkheijm, P., Meijer, E. W., and Schenning, A. P. H. J. Chem. Rev. 2005 105 1491-1546.

Jahnke, E., Lieberwirth, I., Severin, N., Rabe, J. P., and Frauenrath, H. Angew. Chem., Int. Ed. 2006 45 5383-5386.

Li, X. Q., Stepanenko, V., Chen, Z. J., Prins, P., Siebbeles, L. D. A., and Würthner, F. Chem. Commun. 2006 n/a 3871-3873.

Che, Y. K., Datar, A., Balakrishnan, K., and Zang, L. J. Am. Chem. Soc. 2007 129 7234-7235.

Ryu, J.-H., Hong, D.-J., and Lee, M. Chem. Commun. 2008 n/a 1043-1054.

Wang, Q., Lin, T. W., Tang, L., Johnson, J. E., and Finn, M. G. Angew. Chem., Int. Ed. 2002 41 459-462.

Kas, O. Y., Charati, M. B., Kiick, K. L., and Galvin, M. E. Chem. Mater. 2006 18 4238-4245.

Lahann, J., Mitragotri, S., Tran, T. N., Kaido, H., Sundaram, J., Choi, I. S., Hoffer, S., Somorjai, G. A., and Langer, R. Science 2003 299 371-374.

Langer, R. MRS Bull. 2006 31 477-485.

Klok, H. A., Rösler, A., Götz, G., Mena-Osteritz, E., and Bäuerle, P. Org. Biomol. Chem. 2004 2 3541-3544.

Kong, X., and Jenekhe, S. A. Macromolecules 2004 37 8180-8183.

Ashkenasy, N., Home, W. S., and Ghadiri, M. R. Small 2006 2 99-102.

Schmidt, C. E., Shastri, V. R., Vacanti, J. P., and Langer, R. Proc. Natl. Acad. Sci. U.S.A. 1997 94 8948-8953.

Wallace, G., and Spinks, G. Soft Matter 2007 3 665-671.

Lashuel, H. A., LaBrenz, S. R., Woo, L., Serpell, L. C., and Kelly, J. W. J. Am. Chem. Soc. 2000 122 5262-5277.

MacPhee, C. E., and Dobson, C. M. J. Am. Chem. Soc. 2000 122 12707-12713.

Zhang, S. G., Holmes, T., Lockshin, C., and Rich, A. Proc. Nat. Acad. Sci. U.S.A. 1993 90 3334-3338.

Collier, J. H., and Messersmith, P. B. Adv. Mater. 2004 16 907-910.

Haines, L. A., Rajagopal, K., Ozbas, B., Salick, D. A., Pochan, D. J., and Schneider, J. P. J. Am. Chem. Soc. 2005 127 17025-17029.

Smeenk, J. M., Otten, M. B. J., Thies, J., Tirrell, D. A., Stunnenberg, H. G., and van Hest, J. C. M. Angew. Chem., Int. Ed. 2005 44 1968-1971.

Davies, R. P. W., Aggeli, A., Beevers, A. J., Boden, N., Carrick, L. M., Fishwick, C. W. G., McLeish, T. C. B., Nyrkova, I., and Semenov, A. N. Supramol. Chem. 2006 18 435-443.

Wang, W., Wan, W., Zhou, H. H., Niu, S. Q., and Li, A. D. Q. J. Am. Chem. Soc. 2003 125 5248-5249.

Gothard, C. M., Rao, N. A., and Nowick, J. S. J. Am. Chem. Soc. 2007 129 7272-7273.

Cornil, J., dos Santos, D. A., Crispin, X., Silbey, R., and Bredas, J. L. J. Am. Chem. Soc. 1998 120 1289-1299.

Schenning, A., Jonkheijm, P., Peeters, E., and Meijer, E. W. J. Am. Chem. Soc. 2001 123 409-416.

Whitehouse, C., Fang, J. Y., Aggeli, A., Bell, M., Brydson, R., Fishwick, C. W. G., Henderson, J. R., Knobler, C. M., Owens, R. W., Thomson, N. H., Smith, D. A., and Boden, N. Angew. Chem., Int. Ed. 2005 44 1965-1968.

Kayser, V., Turton, D. A., Aggeli, A., Beevers, A., Reid, G. D., and Beddard, G. S. J. Am. Chem. Soc. 2004 126 336-343.

Mesquida, P., Riener, C. K., MacPhee, C. E., and McKendry, R. A. J. Mater. Sci. Mater. Med. 2007 18 1325-1331.

Rubin, N., Perugia, E., Goldschmidt, M., Fridkin, M., and Addadi, L. J. Am. Chem. Soc. 2008 130 4602-4603.

Li, L. S., Jiang, H. Z., Messmore, B. W., Bull, S. R., and Stupp, S. I. Angew. Chem., Int. Ed. 2007 46 5873-5876.

A. Mokhir, B. Zohm, A. Fuessl, R. Kraemer, *Bioorganic & Medicinal Chemistry Letters*, 2003, 13, 2489-2492.

Z. Ni, A. Yassar, T. Antoun, 0. M. Yaghi, *J. Am. Chem. Soc.*, 2005, 127, 12752-12753.

Z. H. Li, M. S. Wong, T. Tao, H. Fukutani, *Org. Lett.*, 2007, 9, 3659-3662 E. N. Durantini, *Synthetic Communications*, 1999, 29, 4201-4222.

J. C. Sancho-García, J. Brédas, D. Beljonne, J. Cornil, R. Martinez-Álvarez, M. Hanack, L. Poulsen, J. Gierschner, H. Mack, H. Egelhaaf, D. Oelkrug, *J. Phys. Chem. B*, 2005, 109, 4872-4880.

J. Hou, Z. Tan, Y. Yan, Y. He, C. Yang, Y. Li, *J. Am. Chem. Soc.*, 2006, 128, 4911-4916.

S. R. Diegelmann, J. M. Gorham, J. D. Tovar, *J. Am. Chem. Soc.*, 2008, 130, 13840-13841.

Mugurama, H., Saito, T., Sasaki, S., Hotta, S., Karube, I. Synthesis and Characterization of α,α'-Bis(aminomethyl) oligo-thiophenes and Their Related Compounds. *J. Heterocyclic Chem.* (1996), 33, (1), 173-8.

Kranich, R., Busemann, A., Bock, D., Schroeter-Maas, S., Beyer, D., Heinemann, B., Meyer, M., Schierhorn, K., Zahlten, R., Wolff, G., Aydt, E. Rational Design of Novel, Potent Small Molecule Pan-Selectin Antagonists. *J. Med. Chem.* 2007, 50, 1101-1115.

B. W. Messmore, J. F. Hulvat, E. D. Sone and S. I. Stupp, *J. Am. Chem. Soc.*, 2004, 126, 14452.

J. Chen and A. J. McNeil, *J. Am. Chem. Soc.*, 2008, 130, 16496.

S. Mahesh, R. Thirumalai, S. Yagai, A. Kitamura and A. Ajayaghosh, *Chem. Commun.*, 2009, 5984.

H. Shao, T. Nguyen, N. C. Romano, D. A. Modarelli and J. R. Parquette, *J. Am. Chem. Soc.*, 2009, 131, 16374.

K. Channon and C. E. MacPhee, *Soft Matter*, 2008, 4, 647.

I. Chemy and E. Gazit, *Angew. Chem. Int. Ed.*, 2008, 47, 4062.

R. A. Miller, A. D. Presley and M. B. Francis, *J. Am. Chem. Soc.*, 2007, 129, 3104.

K. J. Channon, G. L. Devlin, S. W. Magennis, C. E. Finlayson, A. K. Tickler, C. Silva and C. E. MacPhee, *J. Am. Chem. Soc.*, 2008, 130, 5487.

R. Matmour, I. De Cat, S. J. George, W. Adriaens, P. Leclère, P. H. H. Bomans, N. A. J. M. Sommerdijk, J. C. Gielen, P. C. M. Christianen, J. T. Heldens, J. C. M. van Hest, D. W. P. M. Löwik, S. De Feyter, E. W. Meijer and A. P. H. J. Schenning, *J. Am. Chem. Soc.*, 2008, 130, 14576.

A. M. Smith, R. J. Williams, C. Tang, P. Coppo, R. F. Collins, M. L. Turner, A. Saiani and R. V. Ulijn, *Adv. Mater.*, 2008, 20, 37.

L. Ulysse and J. Chmielewski, *Bioorg Med. Chem. Lett.*, 1994, 4, 2145.

E. K. Schillinger, E. Mena-Osteritz, J. Hentschel, H. G. Börner and P. Bäuerle, *Adv. Mater.*, 2009, 21, 1562; D. A. Stone, L. Hsu and S. I. Stupp, *Soft Matter*, 2009, 5, 1990.

M. J. Farrall and J. M. J. Frechet, *J. Am. Chem. Soc.*, 1978, 100, 7998.

P. Rovero, S. Pegoraro, S. Vigano, C. Amato, L. Vaccari, E. Balestreri and R. Felicioli, *Lett. Pept. Sci.*, 1995, 2, 27.

S. Ladame, R. J. Harrison, S, Neidle and S. Balasubramanian, *Org. Lett.*, 2002, 4, 2509.

M. Biernat, P. Stefanowicz, M. Zimecki and Z. Szewczuk, *Bioconjugate Chem.*, 2006, 17, 1116.

F. Würthner, *Chem. Commun.*, 2004, 1564.

M. Cotlet, T. Vosch, S. Habuchi, T. Weil, K. Müllen, J. Hofkens and F. De Schryver, *J. Am. Chem. Soc.*, 2005, 127, 9760.

S. Levin and J. S, Nowick, *J. Am. Chem. Soc.*, 2007, 129, 13043.

F. Freire and S. H. Gellman, *J. Am. Chem. Soc.*, 2009, 131, 7970.

A. Aggeli, M. Bell, N. Boden, J. N. Keen, P. F. Knowles, T. C. B. McLeish, M. Pitkeathly and S. E. Radford, *Nature*, 1997, 386, 259.

Y. Qu, S. C. Payne, R. P. Apkarian and V. P. Conticello, *J. Am. Chem. Soc.*, 2000, 122, 5014.

J. D. Hartgerink, E. Beniash and S. I. Stupp, *Science*, 2001, 294, 1684.

D. J. Pochan, J. P. Schneider, J. Kretsinger, B. Ozbas, K. Rajagopal and L. Haines, *J. Am. Chem. Soc.*, 2003, 125, 11802.

A. Aggeli, I. A. Nyrkova, M. Bell, R. Harding, L. Carrick, T. C. B. McLeish, A. N. Semenov and N. Boden, *Proc. Nat. Acad. Sci. USA,* 2001, 98, 11857.

M. Kasha, H. R. Rawls and M. Ashraf El-Bayoumi, *Pure Appl. Chem.,* 1965, 11, 371.

S. Y. Venyaminov, I. A. Baikalov, C. S. C. Wu and J. T. Yang, *Anal. Biochem.,* 1991, 198, 250.

W. K. Surewicz, H. H. Mantsch and D. Chapman, *Biochem.,* 1993, 32, 389.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A composition comprising one or more π-conjugated oligopeptides having a structure:

peptide-[(organic electronic unit)-peptide]$_n$ wherein:

n is an integer from 1 to 10;

wherein the peptide-[(organic electronic unit)-peptide]$_n$ structure comprises a compound selected from the group consisting of:

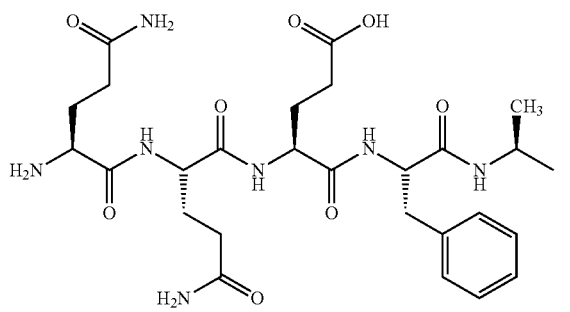

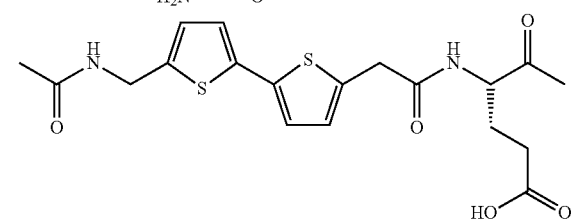

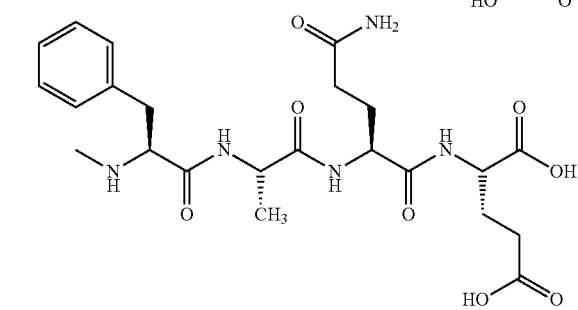

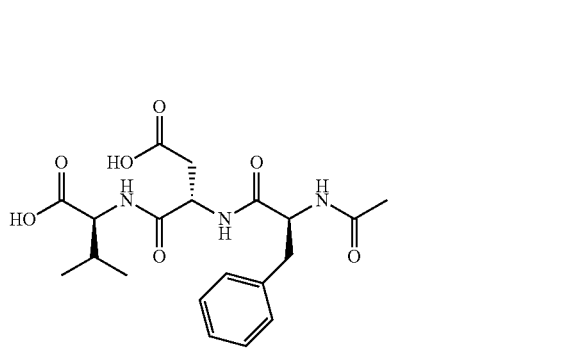

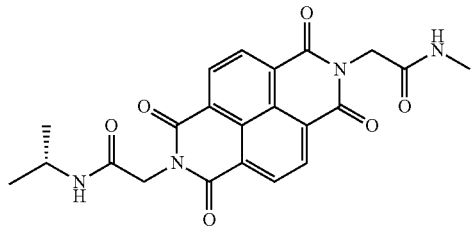

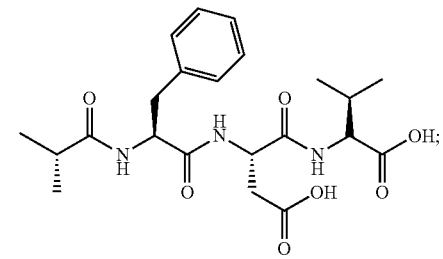

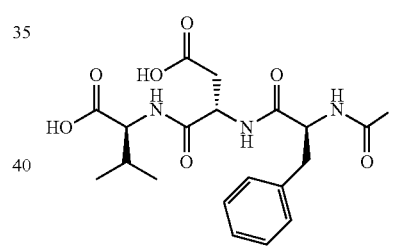

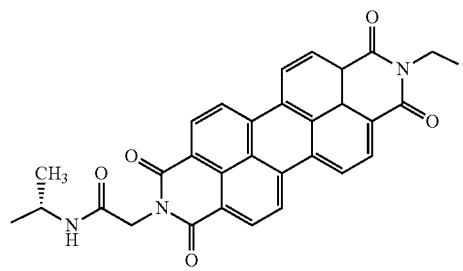

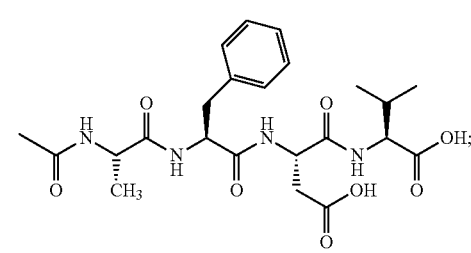

51
-continued

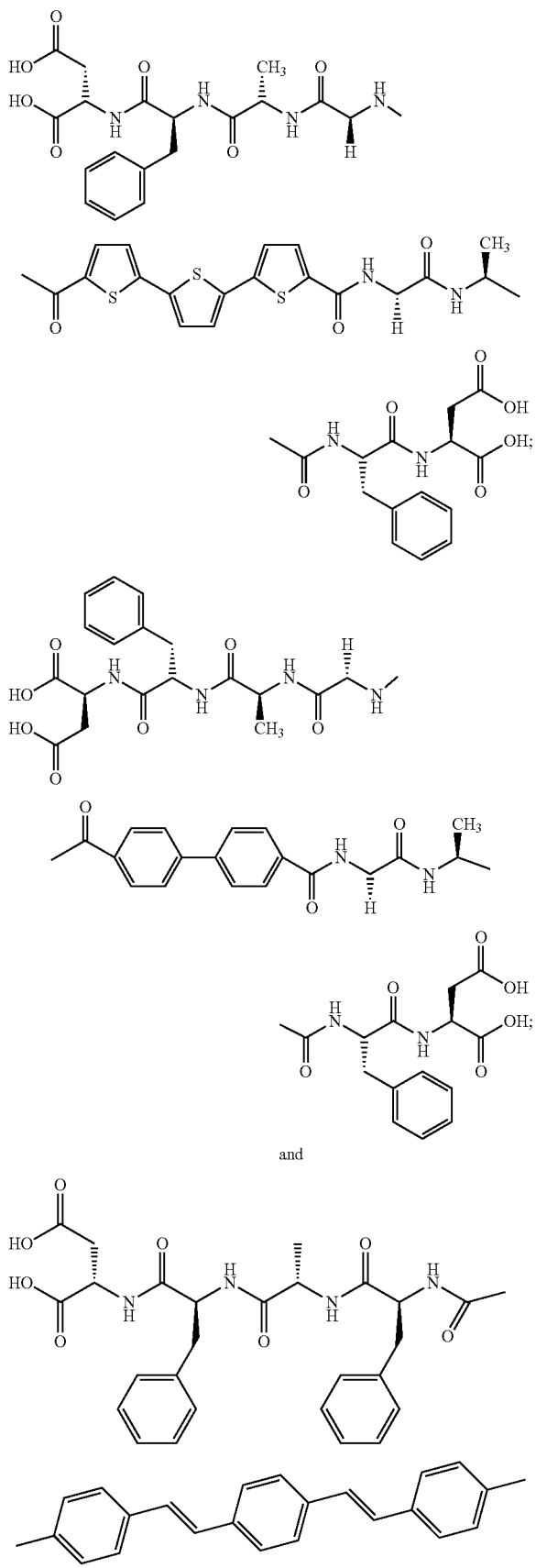

and

52
-continued

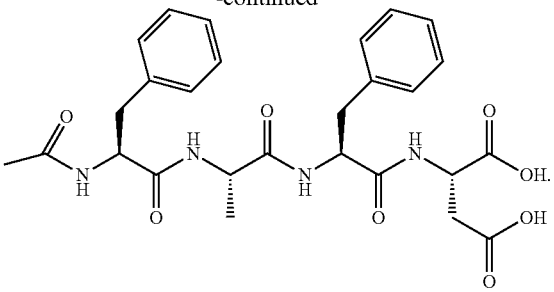

2. A defined nanostructure comprising one or more π-conjugated oligopeptides having a structure:
peptide-[(organic electronic unit)-peptide]$_n$
wherein:
n is an integer from 1 to 10;
the peptide-[(organic electronic unit)-peptide]$_n$ comprises a peptide backbone;
the organic electronic unit is an α-oligothiophene, an oligophenylene, an oligo(phenylene vinylene), a rylene, and diimides and diacids thereof, and wherein the organic electronic unit is embedded in the peptide backbone; and
each peptide can be the same or different and comprises from 2 to 100 naturally occurring amino acid residues or a variant thereof, wherein the peptide backbone comprises two exposed terminal groups and wherein the two exposed terminal groups are a carboxylic acid and an amine or are each a carboxylic acid.

3. The defined nanostructure of claim 2, wherein the nanostructure has at least one sub-10 nm dimension.

4. The defined nanostructure of claim 2, wherein the defined nanostructure comprises π-stacked electronic conduits comprising one or more peptide-[(organic electronic unit)-peptide]$_n$ structures of claim 2.

5. The defined nanostructure of claim 2, wherein the defined nanostructure has a property selected from the group consisting of an electronic property, an optoelectric property, and a cell adhesion property.

6. A cell growth and/or cell adhesion scaffold comprising one or more peptide-[(organic electronic unit)-peptide]$_n$ structures of claim 1.

7. A method of inducing selective tissue growth, the method comprising implanting a cell growth and/or cell adhesion scaffold of claim 6 into a subject, thereby stimulating the adhesion to and proliferation of cells in the location of the scaffold.

8. A method of providing an electrically conductive implant in a subject, the method comprising introducing a defined nanostructure of claim 2 into the subject.

9. A method of obtaining the nanostructure of claim 2, the method comprising admixing a plurality of peptide-[(organic electronic unit)-peptide]$_n$ structures in aqueous solution under conditions such that the nanostructure is formed.

10. The method of claim 9 that is carried out in vitro.

11. The method of claim 9 that is carried out in vivo.

12. An implantable medical device comprising the nanostructure of claim 2.

13. An in vivo biological sensor comprising the nanostructure of claim 2.

14. An in vitro biological sensor comprising the nanostructure of claim 2.

15. An imaging agent comprising the nanostructure of claim 2.

16. A method for preparing a peptide-[(organic electronic unit)-peptide]$_n$ structure of claim 1, the method comprising:
   providing an organic electronic unit comprising a free carboxylic acid moiety and a protected amine moiety; and
   contacting the organic electronic unit with one or more protected amino acids under solid-phase peptide synthesis conditions to obtain the peptide-[(organic electronic unit)-peptide]$_n$.

17. A method of preparing a peptide-[(organic electronic unit)-peptide]$_n$ structure of claim 1, wherein n=1, the method comprising:
   (a) providing one or more peptides immobilized on a solid support, wherein the one or more peptides have a deprotected or free amine group;
   (b) contacting the one or more immobilized peptides with a difunctional diacid or difunctional dianhydride to promote a double imidation or amidation reaction between two immobilized peptides to form a dimer, wherein the diacid or dianhydride forms a linking group; and
   (c) cleaving the dimer from the solid support to obtain the peptide-[(organic electronic unit)-peptide]$_n$ structure.

\* \* \* \* \*

SEQUENCE LISTING

```
<160> NUMBER OF SEQ ID NOS: 6

<210> SEQ ID NO 1
<211> LENGTH: 5
<212> TYPE: PRT
<213> ORGANISM: Artificial Sequence
<220> FEATURE:
<223> OTHER INFORMATION: Peptide

<400> SEQUENCE: 1

Gly Ala Phe Asp Val
1               5

<210> SEQ ID NO 2
<211> LENGTH: 4
<212> TYPE: PRT
<213> ORGANISM: Artificial Sequence
<220> FEATURE:
<223> OTHER INFORMATION: Peptide

<400> SEQUENCE: 2

Gly Ala Phe Asp
1

<210> SEQ ID NO 3
<211> LENGTH: 5
<212> TYPE: PRT
<213> ORGANISM: Artificial Sequence
<220> FEATURE:
<223> OTHER INFORMATION: Peptide

<400> SEQUENCE: 3

Gly Ala Val Glu Val
1               5

<210> SEQ ID NO 4
<211> LENGTH: 4
<212> TYPE: PRT
<213> ORGANISM: Artificial Sequence
<220> FEATURE:
<223> OTHER INFORMATION: Peptide

<400> SEQUENCE: 4

Ala Ala Phe Asp
1

<210> SEQ ID NO 5
<211> LENGTH: 4
<212> TYPE: PRT
<213> ORGANISM: Artificial Sequence
<220> FEATURE:
<223> OTHER INFORMATION: Peptide

<400> SEQUENCE: 5

Phe Ala Phe Asp
1

<210> SEQ ID NO 6
```

-continued

```
<211> LENGTH: 5
<212> TYPE: PRT
<213> ORGANISM: Artificial Sequence
<220> FEATURE:
<223> OTHER INFORMATION: Laminin mimic peptide

<400> SEQUENCE: 6

Ile Lys Val Ala Val
1               5
```